(12) United States Patent
Darnold et al.

(10) Patent No.: US 11,147,725 B2
(45) Date of Patent: Oct. 19, 2021

(54) VALVE ASSEMBLY FOR CUSHION INFLATION

(71) Applicant: ROHO, INC., Belleville, IL (US)

(72) Inventors: Leane Darnold, Kirkwood, MO (US); Kevin Meier, St. Louis, MO (US); Ross Peyton, St. Louis, MO (US); Glenn Fournie, Smithton, IL (US); David Hopp, Edwardsville, IL (US)

(73) Assignee: ROHO, INC., Belleville, IL (US)

( * ) Notice: Subject to any disclaimer, the term of this patent is extended or adjusted under 35 U.S.C. 154(b) by 0 days.

(21) Appl. No.: 16/075,067

(22) PCT Filed: Feb. 6, 2017

(86) PCT No.: PCT/US2017/016678
§ 371 (c)(1),
(2) Date: Aug. 2, 2018

(87) PCT Pub. No.: WO2017/136814
PCT Pub. Date: Aug. 10, 2017

(65) Prior Publication Data
US 2019/0038492 A1    Feb. 7, 2019

Related U.S. Application Data

(60) Provisional application No. 62/291,224, filed on Feb. 4, 2016, provisional application No. 62/291,342, filed on Feb. 4, 2016.

(51) Int. Cl.
*A61G 7/057*    (2006.01)
*A61G 5/10*    (2006.01)
(Continued)

(52) U.S. Cl.
CPC ........ *A61G 7/05769* (2013.01); *A47C 27/082* (2013.01); *A47C 27/083* (2013.01);
(Continued)

(58) Field of Classification Search
CPC ............ A61G 7/05769; A61G 2203/34; A61G 7/05776; A47C 27/083; A47C 27/082;
(Continued)

(56) References Cited

U.S. PATENT DOCUMENTS

| | | | |
|---|---|---|---|
| 3,822,425 A * | 7/1974 | Scales | A61G 7/05769 5/710 |
| 4,541,136 A | 9/1985 | Graebe | |

(Continued)

FOREIGN PATENT DOCUMENTS

| | | |
|---|---|---|
| CN | 203688134 U | 7/2014 |
| WO | 2013010086 A2 | 1/2013 |

OTHER PUBLICATIONS

European Patent Office Extended Search Report for Application No. 17748337.7 dated Aug. 1, 2019 (7 pages).

(Continued)

*Primary Examiner* — Atif H Chaudry
(74) *Attorney, Agent, or Firm* — Michael Best & Friedrich LLP

(57) ABSTRACT

The present disclosure generally relates to a manifold valve assembly engaged to an inflatable apparatus, such as a cushion to prevent pressure ulcers, for example. The manifold valve assembly is also in communication with a processing device to determine an optimal immersion level for a user seated on the inflatable apparatus. Additionally the processing device, in communication with the manifold valve assembly may save optimal immersion or air pressure levels for comparison to future checks of cushion pressure and send that to a user interface at the processing device. The assembly and processing device may also save and dis play a history of pressure checks.

13 Claims, 35 Drawing Sheets

(51) Int. Cl.
*G01L 17/00* (2006.01)
*A47C 27/08* (2006.01)
*A47C 27/10* (2006.01)
*G16H 20/30* (2018.01)
*G16H 40/40* (2018.01)
*G16H 40/63* (2018.01)
*G05B 15/02* (2006.01)

(52) U.S. Cl.
CPC .......... *A47C 27/10* (2013.01); *A61G 5/1043* (2013.01); *A61G 5/1045* (2016.11); *A61G 5/1091* (2016.11); *A61G 7/05776* (2013.01); *G01L 17/00* (2013.01); *G16H 20/30* (2018.01); *G16H 40/40* (2018.01); *G16H 40/63* (2018.01); *A61G 2203/20* (2013.01); *A61G 2203/34* (2013.01); *G05B 15/02* (2013.01); *Y10T 137/3584* (2015.04); *Y10T 137/3662* (2015.04); *Y10T 137/3724* (2015.04); *Y10T 137/8326* (2015.04)

(58) Field of Classification Search
CPC .............. A47C 27/10; Y10T 137/3724; Y10T 137/3584; Y10T 137/3662; Y10T 137/8326
See application file for complete search history.

(56) References Cited

U.S. PATENT DOCUMENTS

| | | | |
|---|---|---|---|
| 6,415,814 B1* | 7/2002 | Hand | A61G 7/05776 137/487.5 |
| 7,414,536 B2 | 8/2008 | Call et al. | |
| 2003/0138329 A1* | 7/2003 | Koyano | G08B 21/14 417/63 |
| 2003/0192125 A1* | 10/2003 | Graebe | A47C 27/081 5/710 |
| 2005/0210993 A1 | 9/2005 | Toyoda et al. | |
| 2010/0120362 A1 | 5/2010 | Walley et al. | |
| 2012/0105233 A1 | 5/2012 | Bobey et al. | |
| 2013/0284274 A1 | 10/2013 | Chaffee | |
| 2014/0007656 A1 | 1/2014 | Mahoney | |
| 2014/0047645 A1 | 2/2014 | Choi et al. | |
| 2014/0259430 A1 | 9/2014 | Rickman et al. | |
| 2014/0259434 A1 | 9/2014 | Nunn et al. | |
| 2015/0000044 A1* | 1/2015 | Morimura | A47C 27/083 5/710 |
| 2016/0022521 A1 | 1/2016 | Darnold et al. | |
| 2016/0317370 A1* | 11/2016 | Evans | A61G 7/05776 |
| 2017/0239131 A1* | 8/2017 | Brzenchek | A61H 9/0078 |
| 2018/0280219 A1* | 10/2018 | Garrett | A61G 7/001 |

OTHER PUBLICATIONS

European Patent Office Extended Search Report for Application No. 17748339.3 dated Sep. 12, 2019 (5 pages).
International Search Report and Written Opinion for Application No. PCT/US2017/016678 dated Jun. 9, 2017 (11 pages).
International Search Report and Written Opinion for Application No. PCT/US2017/016687 dated Apr. 21, 2017 (8 pages).

* cited by examiner

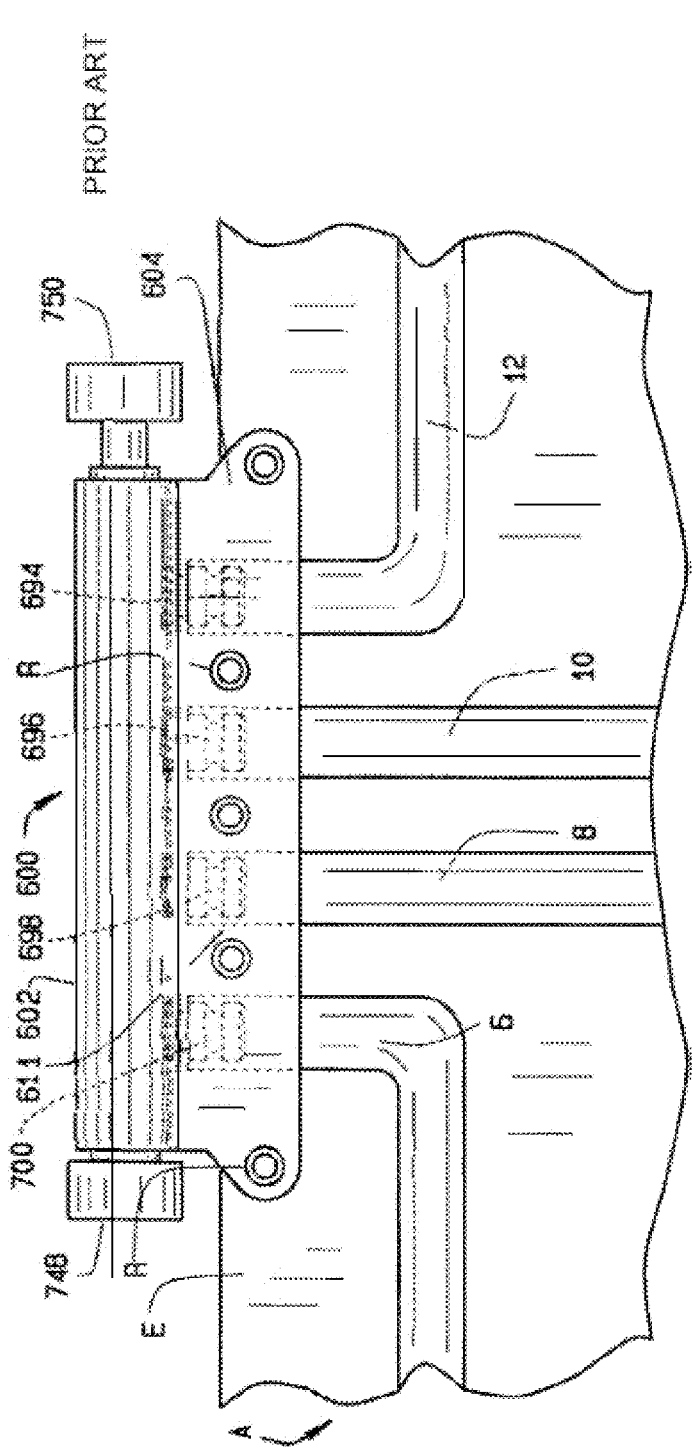
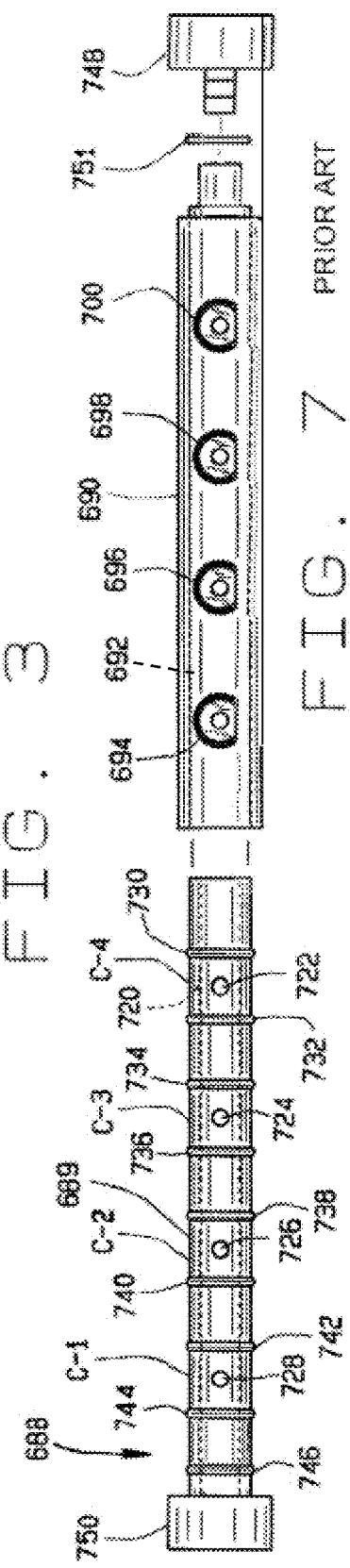

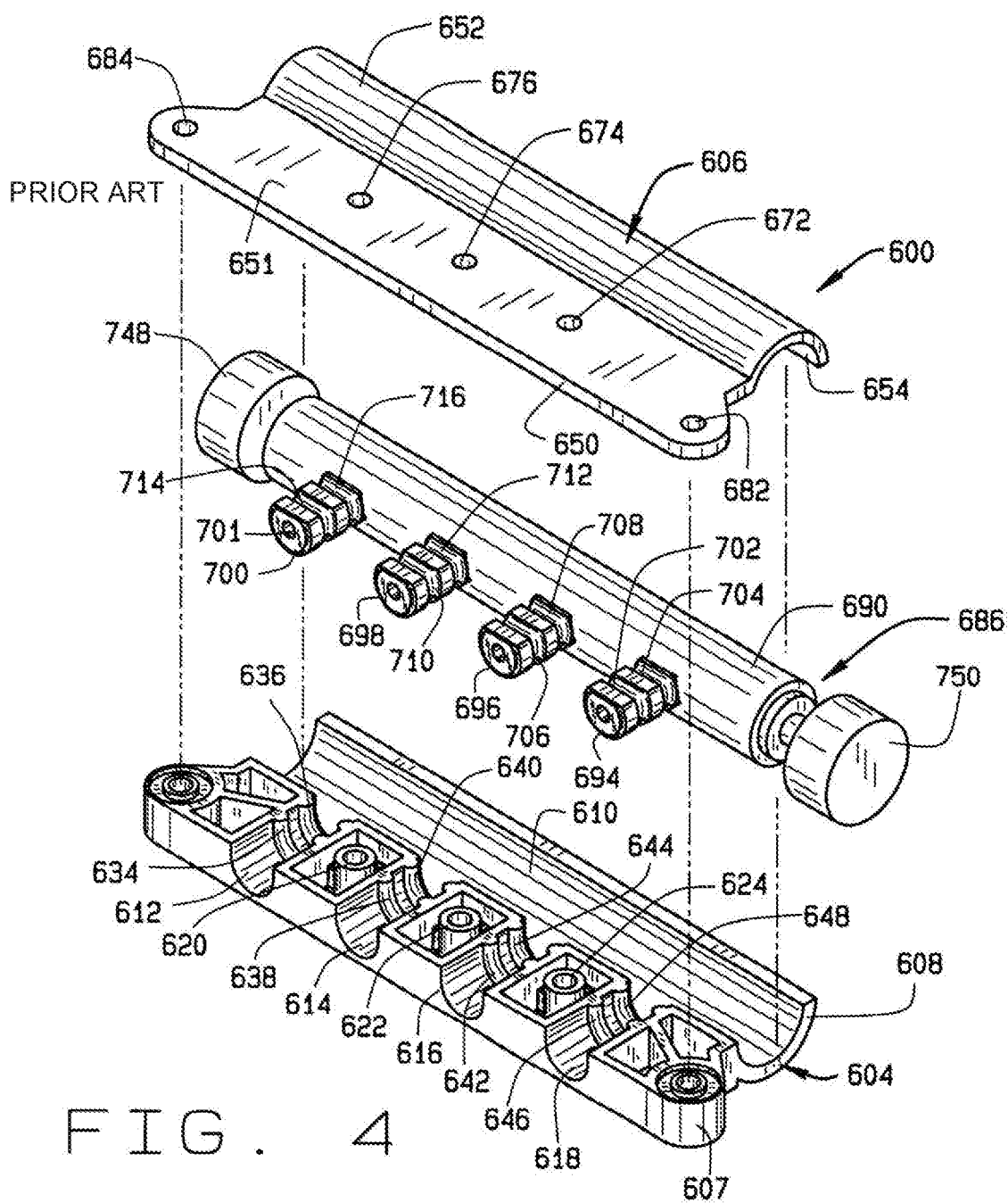
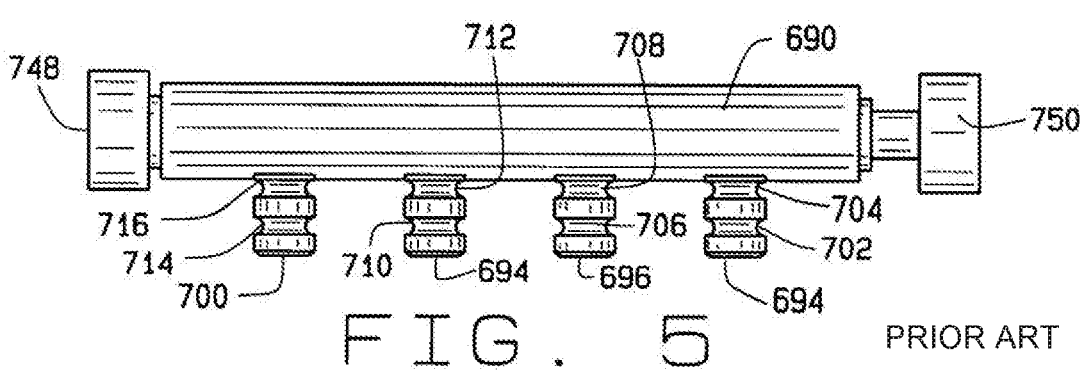

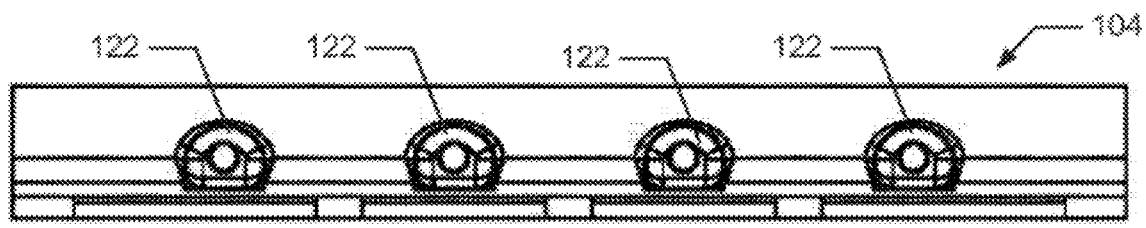
FIG. 18
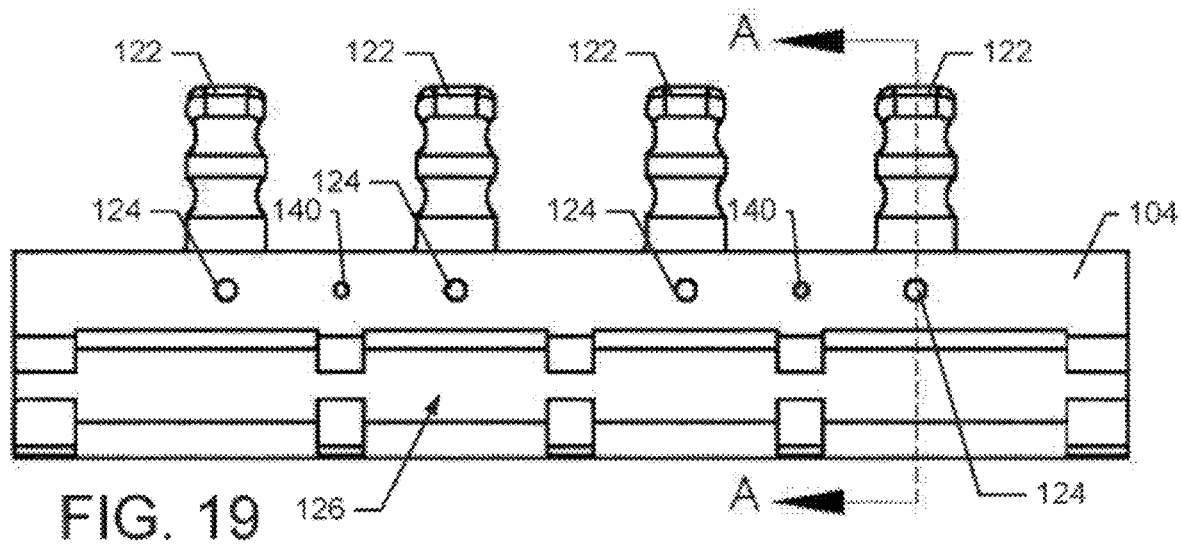
FIG. 19
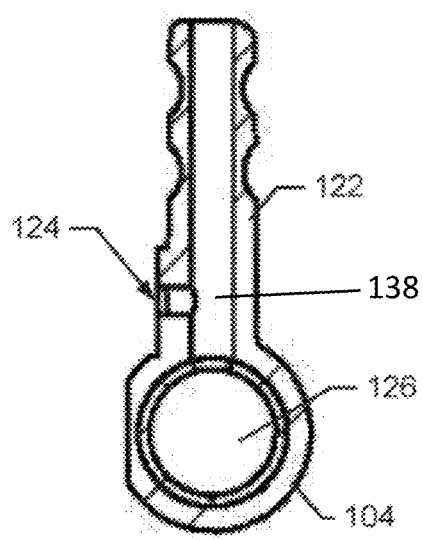
SECTION A-A  FIG. 20

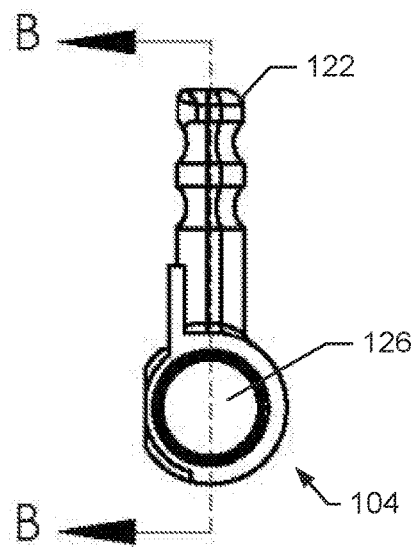
FIG. 21
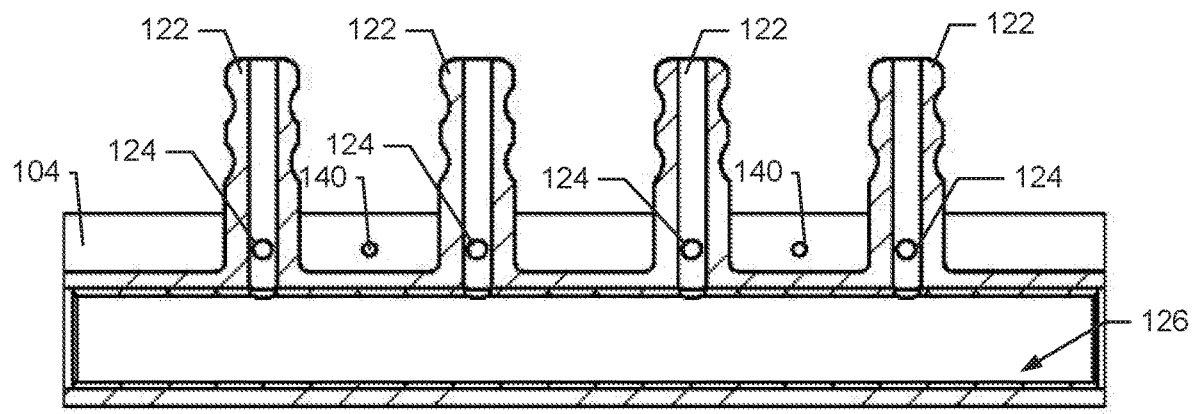
SECTION B-B    FIG. 22

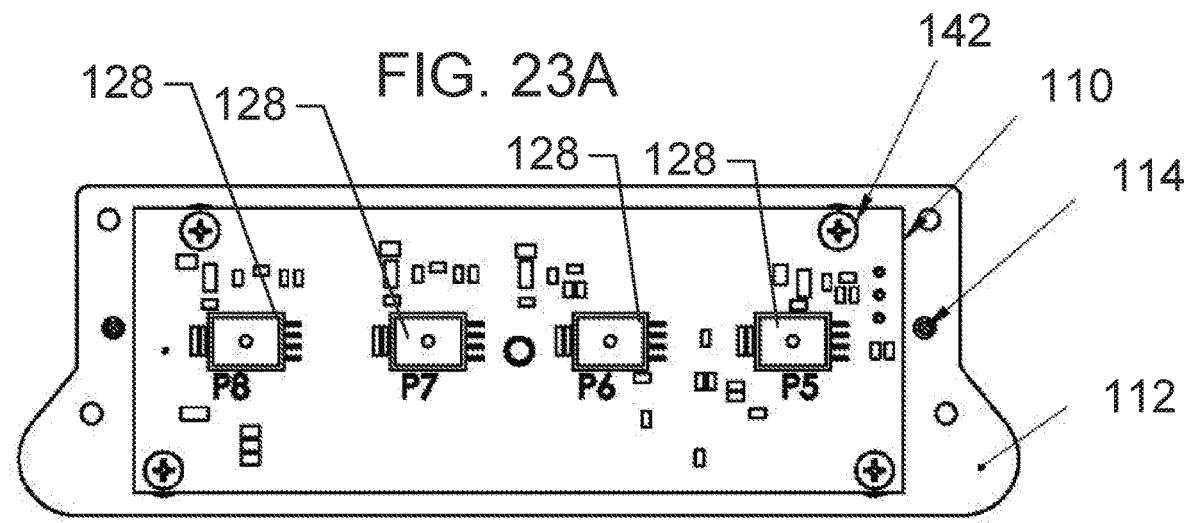
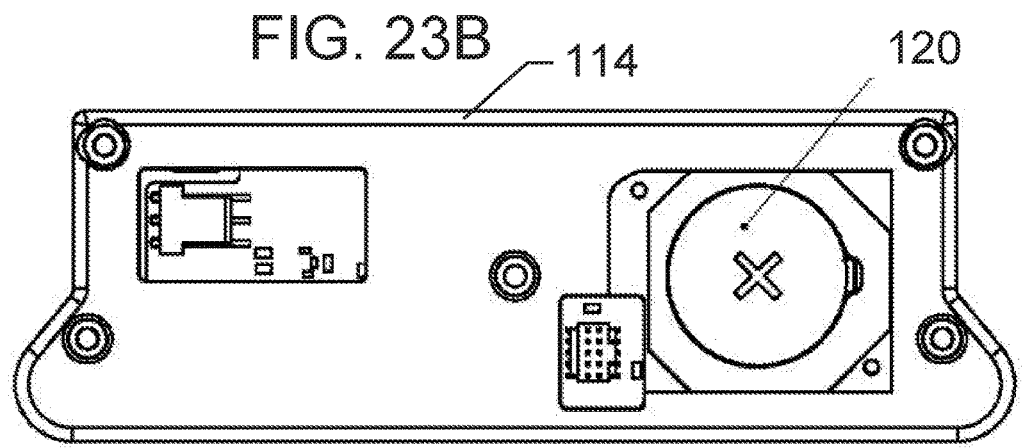
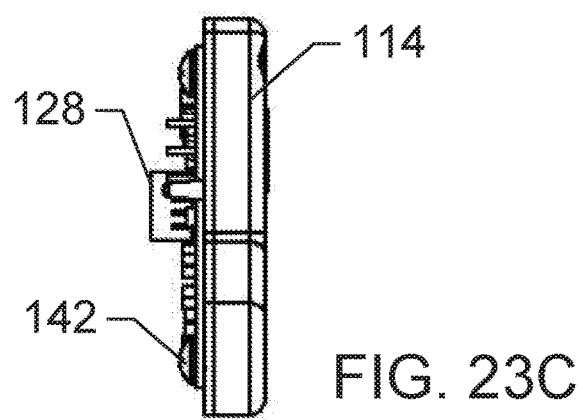

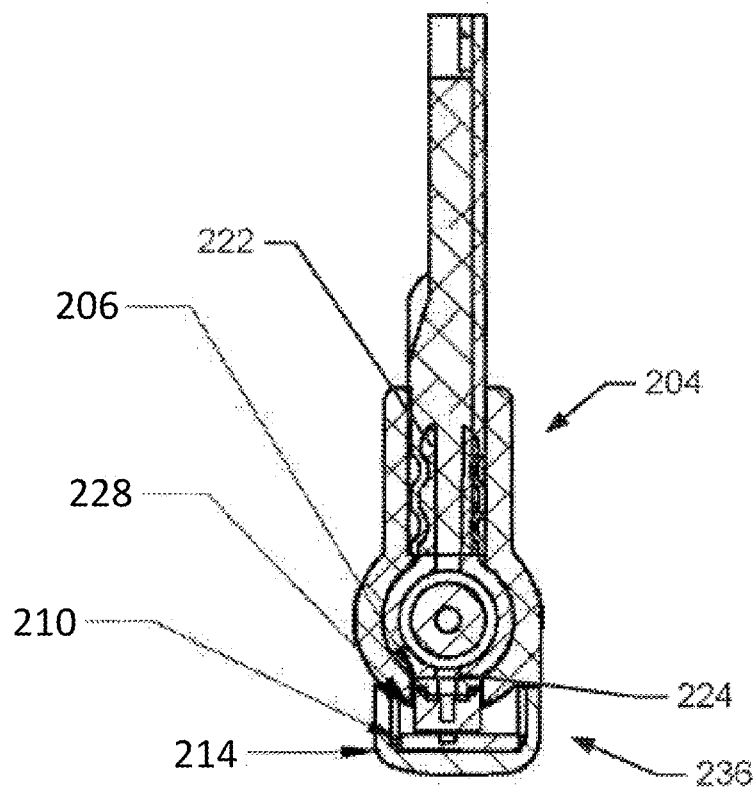
FIG. 25C   SECTION D-D
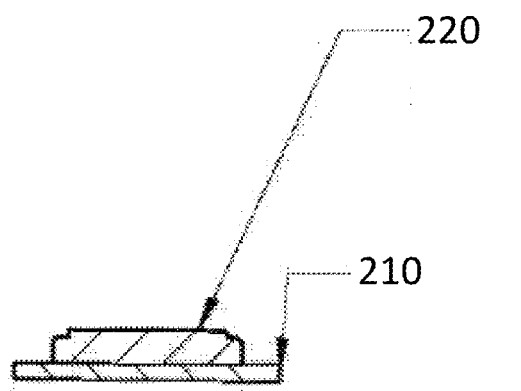
FIG. 25D

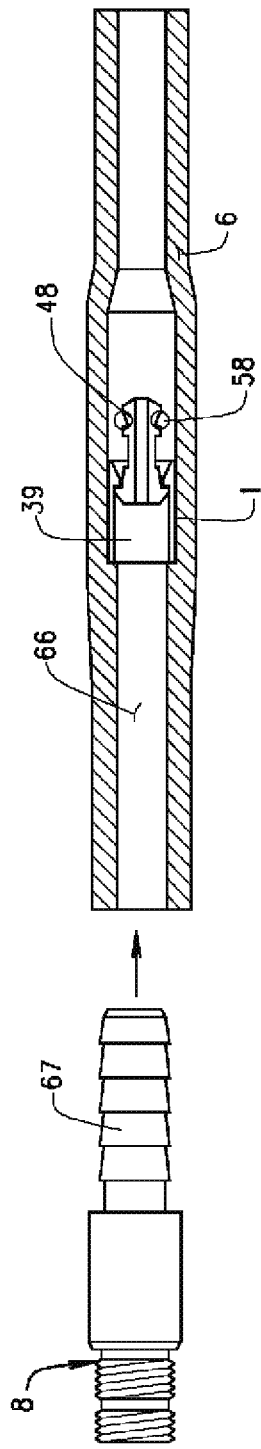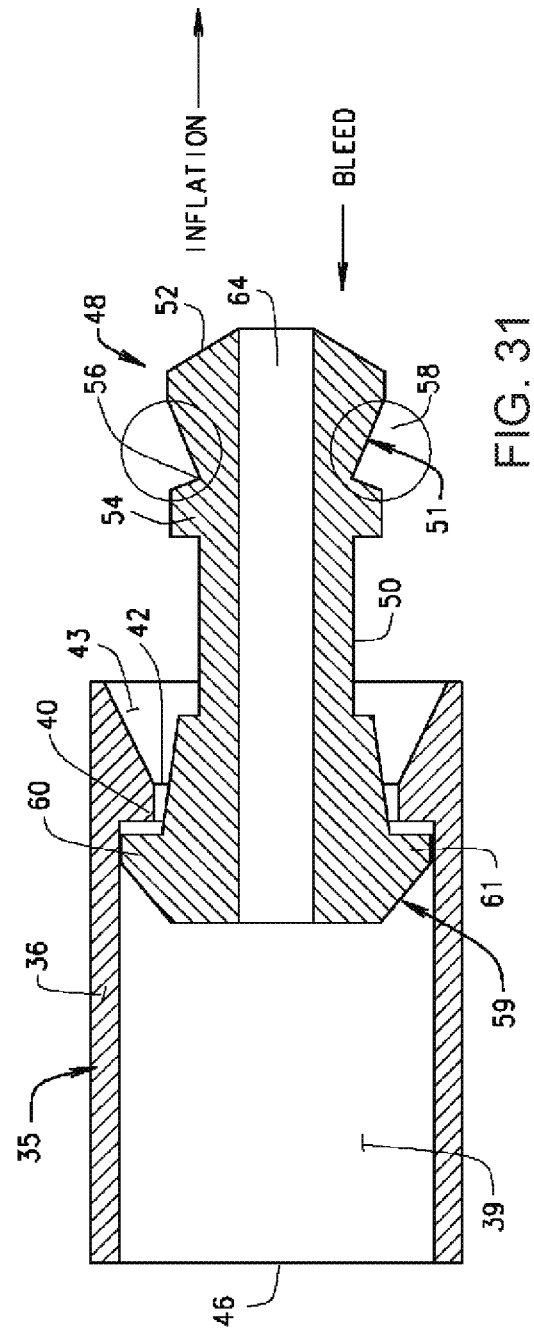

SECTION F-F

SECTION G-G

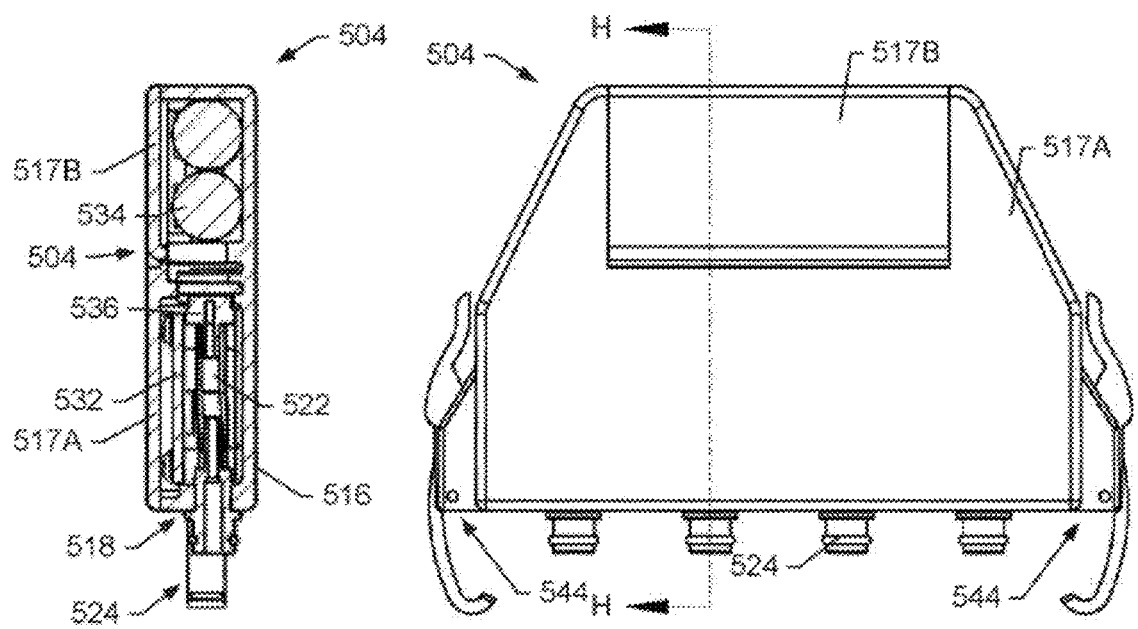
FIG. 42B
FIG. 42A
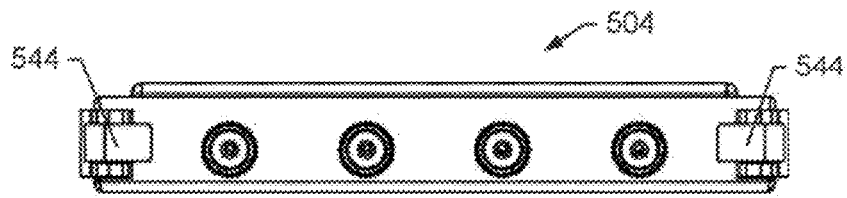
FIG. 42C
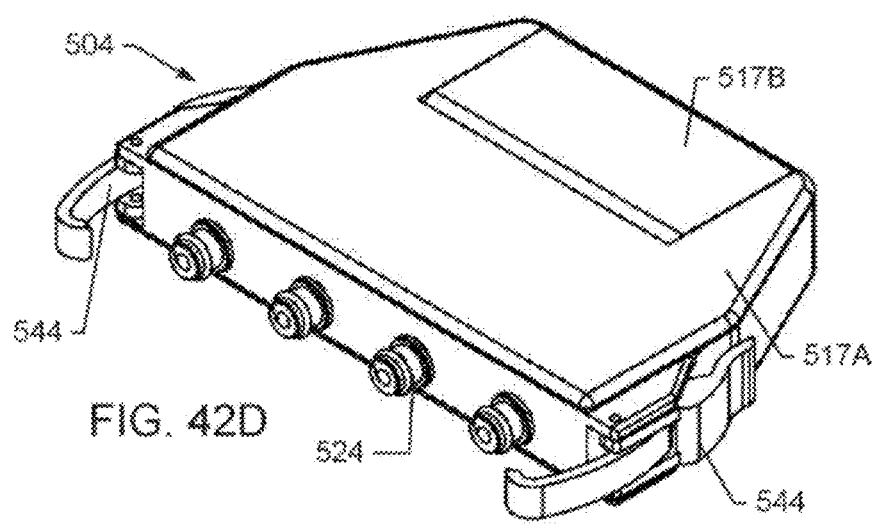
FIG. 42D

VALVE ASSEMBLY FOR CUSHION INFLATION

CROSS REFERENCE TO RELATED APPLICATIONS

This application is a national phase filing of International Patent Application No. PCT/US2017/016678, entitled "Valve Assembly for Cushion Inflation" and filed on Feb. 6, 2017, which claims priority to U.S. Provisional Patent Application No. 62/291,342, entitled "Valve Assembly for Cushion Inflation" and filed on Feb. 4, 2016, and to U.S. Provisional Patent Application No. 62/291,224, entitled "System and Method for Cushion Inflation" and filed on Feb. 4, 2016, the entire contents of each application is herein incorporated by reference in its entirety.

The present application is also related to U.S. Pat. No. 6,687,936, which issued on Feb. 10, 2004, and is incorporated herein by reference in its entirety. In addition, this application is related to U.S. application Ser. No. 14/435,812, filed Apr. 15, 2015, entitled "Cushion Immersion Sensor and International Patent application No. PCT/US2014/066182, filed Nov. 18, 2014, entitled "Reduced Outflow Inflation Valve," that further claims priority to U.S. Provisional Patent Application No. 61/933,021 filed on Jan. 29, 2014, each of which is incorporated herein by reference.

BACKGROUND

Air cell cushions are used by individuals who must remain seated for extended periods of time, for example, a disabled individual who uses a wheelchair for locomotion. Cellular cushions provide the most uniform distribution of weight and thus provide the greatest protection from the occurrence of pressure sores. These cushions have an array of closely spaced air cells that project upwardly from a common base. Within the base the air cells communicate with each other, and thus, all exist at the same internal pressure. Hence, each air cell exerts essentially the same restoring force against the buttocks, irrespective of the extent to which it is deflected.

Conventionally, proper immersion within a cushion has been determined by a hand check method. The user inserts a hand between the body and cushion to determine when the user is properly immersed in the cushion. This is a subjective measurement and the depth of immersion can vary depending on who is checking immersion depth. Thus, it is prone to inaccurate measurement and error. Additionally, hand checking the level of immersion is time-consuming, complex, and especially difficult for heavy users to slide hand under person to check.

SUMMARY

The present invention is an improvement on manifold valves required by zoned cellular cushions. Heretofore, the zoned cushions employed integral channels which lead from the several zones and which are connected through an integral common manifold and associated valve. In particular, the present disclosure relates to a manifold valve apparatus that includes or is at least in communication with pressure sensors and communication devices to allow for the remote observation and control of the zoned cellular cushions. It is with these issues in mind, among others, that various aspects of the disclosure were conceived.

According to one aspect, valve assembly for cushion inflation includes a manifold valve assembly including one or more pressure transducers and a data transmission device. In one aspect, the valve assembly further includes a processor, memory, and the data transmission device may also receive data. The manifold valve assembly is used with an inflatable apparatus having a base and an array of upstanding fluid filled cells on one side of the base, the array of cells being divided into a plurality of inflation zones, each zone having a separate zone air conduit extending from the zone.

In an aspect, the valve assembly includes a manifold valve. In this aspect, the manifold valve includes a valve casing defining a slide housing seat, a slide housing disposed within the slide housing seat, at least one transducer bore in the slide housing, a gasket engaged to an exterior of the slide housing, a slide within the slide housing bore, and an electronics enclosure engaged to the slide housing. In one aspect, the electronics enclosure may house at least one pressure transducer in fluid communication the at least one zone air conduit, at least one processor, at least one transceiver, and a power source. The slide housing may be in fluid communication with each zone air conduit and the transducer bore may be in fluid communication with at least one zone air conduit. In an aspect, the gasket defines at least one gasket aperture, the at least one gasket aperture is aligned with the at least one transducer bore, and the slide housing defines at least one sensor port, the at least one sensor port co-aligned and in fluid communication with the at least one transducer bore through the at least one gasket aperture.

In other aspects, the manifold valve may be removably engaged to the inflatable apparatus. The electronics enclosure may be removably engaged to the manifold valve, and when the electronics enclosure is detached from the valve assembly, an enclosure comprising at least one sealing gasket to seal each of the zone air conduits may be engaged to the manifold valve. In yet another aspect, the slide housing may further include a longitudinal bore and at least one connector having an inner bore for fluid communication between at least one zone air conduit and the slide housing longitudinal bore. The slide housing may also further include a wall creating a longitudinal bore and at least one opening through the slide housing wall into the longitudinal bore. Movement of the slide within the longitudinal bore to a first position may place the at least one slide opening in functional alignment with the at least one connector thereby opening the valve, and movement of the slide within the longitudinal bore to a second position may place the at least one slide opening out of functional alignment with the at least one connector thereby closing the valve.

In an aspect, at least one or the transceiver and the processor may be a Bluetooth low energy device. The electronics enclosure may further include a memory. In another aspect, the at least one processor may transmit an indication of pressure in the cushion and store received data from App that indicates optimal immersion depth. In this aspect, the processor may detect an optimal immersion depth in response to a signal received from the at least one pressure transducer, and the signal may correspond to a change in air pressure in at least one zone air conduit. The electronics enclosure may also include one or more other gaskets.

The at least one pressure transducer may detect air pressure changes in range of between 0 Pascal (0 mmHg) and 13332.2 Pascal (100 mmHg) and may be configured to detect an air pressure change of at least 33.3306 Pascal (0.25 mmHg). In an aspect, the manifold valve may further include one or more visual indicators.

According to another aspect, method for using a manifold valve assembly includes providing the valve assembly, inflating the plurality of inflation zones, positioning a user on the inflatable apparatus, releasing air from at least one inflation zone, determining at another processor in communication with the valve processor, if an optimal immersion level is achieved by comparing pressure data received from the pressure transducer to an algorithm in an app, and generating a signal at the processor to actuate a visual indicator. In an aspect, the valve assembly includes a manifold valve, an integrated pressure transducer, a valve processor, and a transceiver. Air released from the at least one inflation zone may be released through a reduced out-flow valve.

In an aspect, the method of using the manifold valve may further include releasing air from at least one other inflation zone to reach the optimal immersion level and actuating the manifold valve to lock a desired volume of air in at least one of the inflation zones once the optimal immersion level has been reached. In yet another aspect, the method may also include observing the visual indicator to determine the optimal immersion level and ceasing the release of air from the at least one inflation zone.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment.

FIGS. 1-12 are views of a valve assembly for zoned cellular cushions according to various embodiments.

FIGS. 18-22 are views of a slide housing of the manifold valve assembly for zoned cellular cushions according to one embodiment.

FIGS. 23A-E depict orthographic views of various electronic components of the manifold valve assembly for zoned cellular cushions according to one embodiment.

FIGS. 25A-D are views of another manifold valve assembly for zoned cellular cushions including electronic components according to one embodiment.

FIG. 30 is an exploded side elevation view of the inflation valve and tubing with the tubing and reduced outflow valve in cross-section.

FIG. 31 is an enlarged cross-sectional view of the reduced outflow valve in an outflow restricted position.

FIG. 42A is bottom plan view of a detachable electronics assembly, according to one embodiment.

FIG. 42B is a cross-section view of the detachable electronics assembly as viewed along line H-H of FIG. 41A.

FIGS. 42C and 42D are a front view and perspective view, respectively, of the detachable electronics assembly of FIG. 42A.

DETAILED DESCRIPTION

The manifold valve system of the present disclosure includes improvements, additional functionality, and additional features over other zoned cellular cushions, including but not limited to that disclosed in U.S. Pat. No. 6,687,936 (The '936 Patent) and related patents and patent applications, each of which is incorporated herein by reference in their entireties. In one aspect, the manifold valve assembly of the present application includes many of the same features as the valve disclosed in the '936 Patent; however the present manifold valve assembly also includes a number of new structures and features that permit access and evaluation of the pressure values in an associated zoned cellular cushion.

For example, an embodiment of manifold valve assembly of the present disclosure incorporates at least one pressure transducer in a novel structural arrangement to determine the immersion level of a user seated in the zoned cellular cushion. The present manifold valve assembly also incorporates one or more electronic computational systems, including a processor and memory to permit electronic communication and manipulation of the cushion. In yet another aspect, the electronic systems may be detached from the manifold valve assembly in order to facilitate cleaning or maintenance of the cushion, the manifold valve assembly, or the electronic components detached therefrom.

Figure 1:
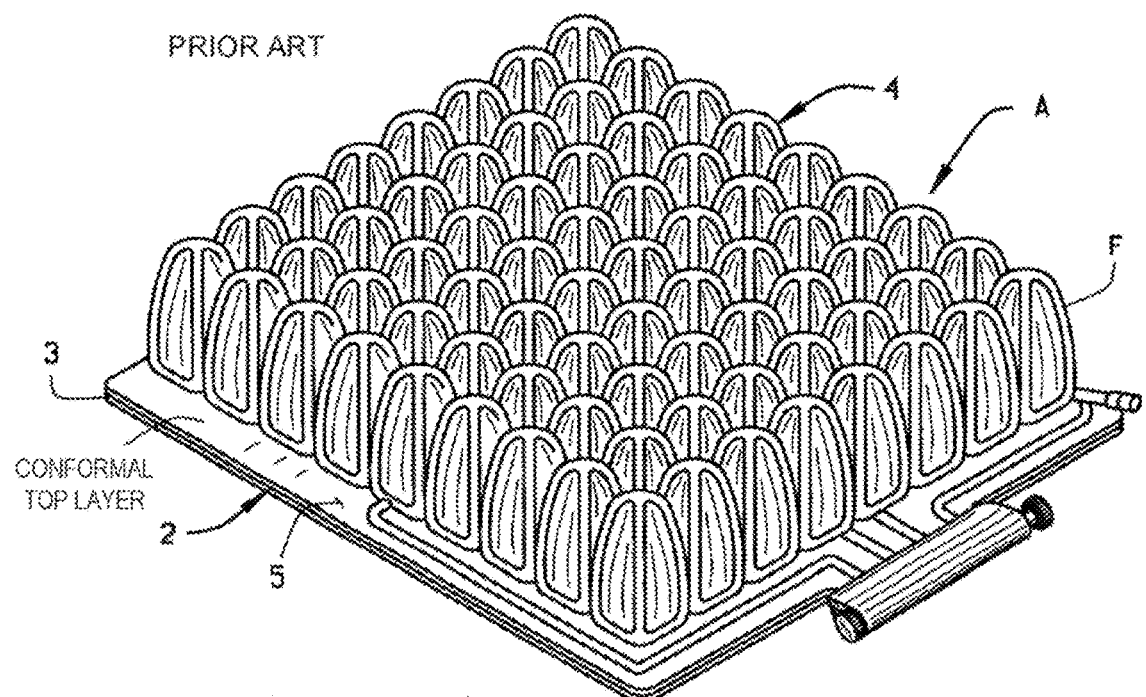
Figure 2:
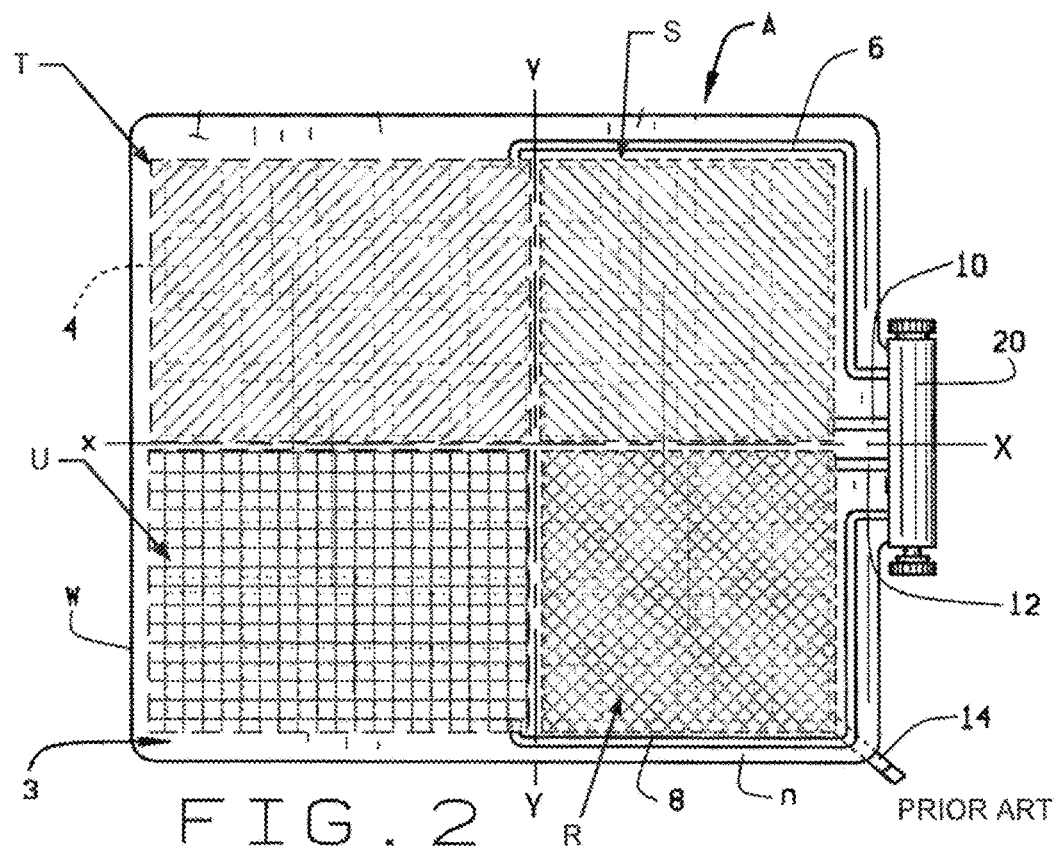
Figure 6:
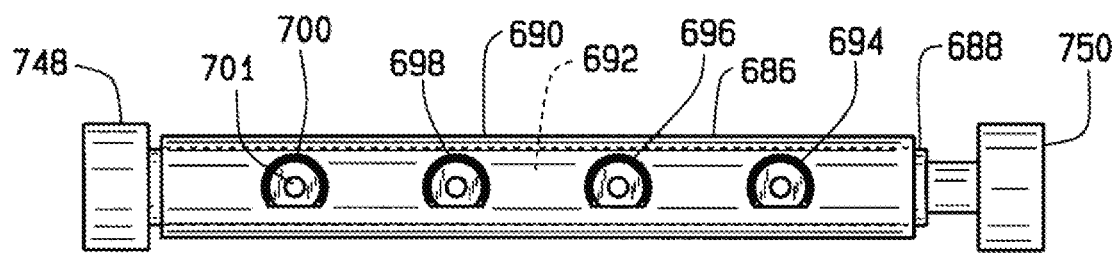

FIGS. 1A-B display example zoned cellular cushions that may be used with the new manifold valve assembly of the present disclosure. According to various embodiments, the zoned cellular cushion is substantially similar to cushion apparatus described in the '936 Patent. In one aspect, the zoned cellular cushion 1 may include a cellular cushion which is highly flexible and is designed for use on an underlying supporting surface, such as the seat of a wheelchair, the seat of a vehicle or the seat of a conventional chair. Being cellular, the cushion 1 distributes the weight of its occupant generally uniformly over the entire area of the buttocks and thereby distributes the pressures resulting from the supported weight of the ischia, that is, the bony prominence of the buttocks. It further has the capacity to position and stabilize the user. It will be appreciated that although the present invention is described as employed on a cushion, the novel valve assembly can also be employed with an air mattress or air mattress section or other similar devices that include inflatable zones.

According to various embodiments, the cushion 1 may include a base 2 and air cells 4 that project upwardly from the base 2. Generally the air cells 4 are molded as a conformal having a web 5 interconnecting the cells 4. The base is comprised of the web and a backing 3. Both the backing 3 and the air cells 4 preferably can be molded or otherwise formed from a highly flexible neoprene. The cells 4 and web 5 may be formed using any suitable method. On the other hand, the air cells 4 can be molded from a highly flexible neoprene and the base 2 can be vacuum formed of the web and a backing formed from polyurethane, for example, and appropriate! y attached to the conformal.

The base 2 generally is rectangular and the cells 4 are arranged on it in longitudinal and transverse rows, with each cell occupying both a longitudinal and a transverse row. It will be appreciated that although the illustrated embodiment provides for individual cells each having a configuration consisting of four fins F, the configuration of the individual cells is incidental to the invention. The present invention can be used with a cushion employing any preferred configuration of cells 4 that is, for example, cells having any number of fins or sides, cells having no fins, for example, cylindrical, cubical cells or rounded cells.

The cells 4 are further arranged in zones, typically four zones R, S, T, and U. The zones R and S lie side by side at the front of the cushion I and the zones T and u exist side by side at the rear of the cushion 1. The right zones R and u are separated from the left zones S and T along a longitudinal axis x, whereas the front zones R and S are separated from the rear zones T and u along a transverse axis y. More or fewer zones and differing arrangements of those zones may be employed.

Within the base 2 the cells 4 of the zone R communicate with each other, so that all exist at the same general internal pressure irrespective of how far any individual cell is depressed. The same holds true with regard to the cells 4 of the zone s, the cells 4 of the zone t, and the cells 4 of the zone U. In other words, the cells 4 of zone Rare normally isolated from the cells of the remaining zones s, t, and u. Likewise, the cells 4 of the zone S are normally isolated as are the cells 4 of zones R, T and u and so forth. Thus, the cells 4 of each zone R, S, T, and U collectively define a separate inflation zone or compartment.

A fluid conduit 6 extends from zone T toward the front of the cushion. Likewise a fluid conduit 8 extends from zone U to the front of the cushion. Two shorter conduits 10 and 12 extend from zones S and R respectively toward the front of the cushion. The conduits 6, 8, 10 and 12 all terminate near an edge of the cushion and are in fluid communication with the cushion valve of the present invention, as will be explained in detail below. It also will be appreciated that the various conduits can be formed in any appropriate manner without departing from the scope of the invention. For example, the conduits can be formed integrally in the base 2 when the base is molded or vacuum formed.

The illustrated embodiment is one acceptable configuration of conduits. The conduits can be formed in any acceptable manner that results in access to the conduits at one location on the periphery of the cushion so that valve of the present invention can be utilized. By way of example, the conduits can be formed into the web 5 or may comprise separate tubing without departing from the scope of the invention. An air filling valve 14 is located at zone R that is opened and closed simply by turning its end. It will be appreciated, however, that the air fill valve can be located at any desirable and convenient location on the cushion.

The conduits 6, 8, 10 and 12 are operatively connected to a valve assembly 600, which is one primary aspect of the present invention. As will be explained in detail hereinafter, when closed, the valve assembly 600 isolates the cells 4 of the several zones R, S, T, and U. But when opened, it interconnects the zones R, S, T, and U, so that the interiors of all the cells 4 in all zones are in communication and, therefore, all exist at the same internal pressure. The air filling valve 14 enables air to be pumped into the cells 4 of the zone in which it is located and, when the valve assembly 600 is open, the air inflates the cells 4 of all of the zones R, S, T and U. Use of only one air-filling valve 14 insures all of the cells 4 in the zones R, S, T, and U will be at the same initial pressure, even though the volume of air in the cells or zones may vary in use.

While cushion A and the novel valve are designed for seat cushions, they may be expanded in use and, as previously discussed, configured differently in the arrangement of the zones or the number of zones. Further, the same inventive principles can be applied to inflatable mattress, auto, truck, bicycle or motorcycle seat cushions or any other type of air cushioned seating or resting surface. Consequently, the term "cushion" as used in the appended claims is intended to include any such seating apparatus, regardless of configuration or application. Moreover, the novel valve may be employed in any air inflated device, other than cushions, which is divided in to air chambers or zones.

FIGS. 3-12 depict one embodiment of an example valve assembly 600 for a zoned cellular cushion. The following description is provided to illustrate many of the basic components and functionality of the presently disclosed manifold valve assembly 100. The novel and inventive features of the present manifold valve assembly 100 will be discussed more fully below with reference to FIGS. 13-23.

The exemplary valve assembly 600 is indicated generally by reference numeral 600. Valve 600 includes novel attachment and sealing features, which now will be explained in detail. As seen in FIG. 3, valve 600 is attached to the peripheral edge E of a cushion that includes four air conduits 6, 8, 10 and 12 which are in fluid connection with the zones R, S, T and U, as previously explained. Valve 600 includes an outer casing 602 comprising two halves or sections 604 and 606.

Figure 8:
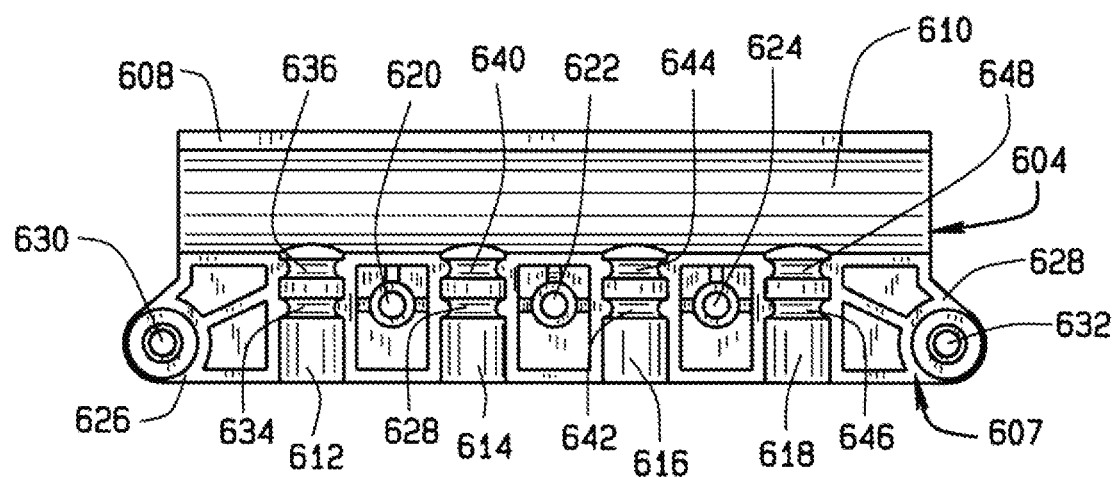
Figure 9:
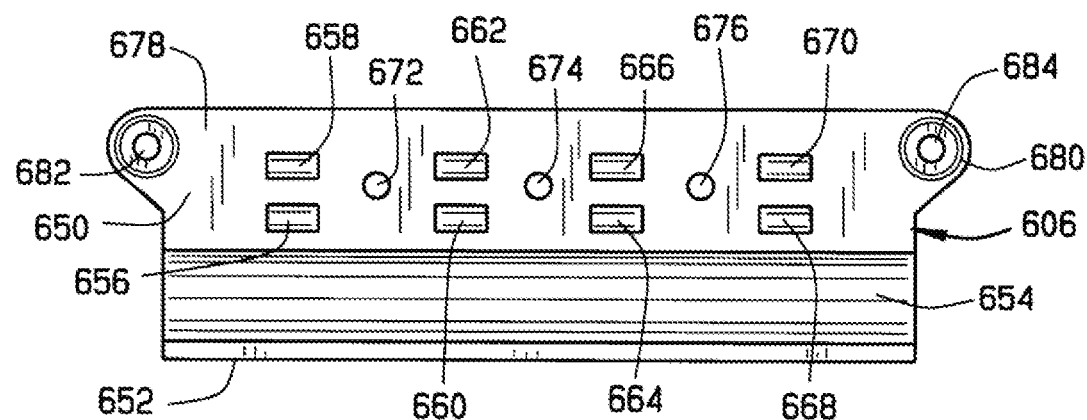

Referring to FIGS. 4 and 8, section 604, which generally is the top section when attached to a cushion as shown in FIG. 3, has a forward segment 607 and a rear segment 608 that has a generally semi-circular cross section that defines a trough 610 that extends the length of the section. Forward section 607 has a generally greater material thickness than the rear segment, has a substantially flat outer surface 611 (FIG. 3). The inside of segment 607 has a series of equally spaced nipple connector seats comprised of depressions 612, 614, 616 and 618 in the material thickness and, in the embodiment shown, having a semi-circular cross section which are perpendicular to trough 610. In between the nipple seats are series of three equally spaced mounting holes 620, 622, 624. At one end of segment 607 is a wing 626 and at the opposite end is wing 628. Mounting holes 630 and 632 are formed in wings 626 and 628, respectively. Nipple seat 612 has a pair of spaced apart raised detents 634 and 636 formed on the surface. Likewise, nipple seat 614 includes raised detents 638, 640, nipple groove 616 includes raised detents 642, 644, and nipple seat 618 has raised detents 646, 648.

Casing half 606 has forward segment 650 which is substantially flat and rear segment 652 having a generally semi-circular cross section defining a trough 654. The overall shape of casing half 606 is complementary to that of casing half 604. The inside surface 655 of forward segment 650 has four pairs of spaced apart raised detents, 656, 658; 660, 662; 664, 666; and 668, 670. Forward segment 650 includes three equally spaced mounting holes 672, 674, 676 between the pairs of raised detents. Segment 650 includes wings 678 and 680 with mounting holes 682, 684, respectively formed therein. It will be noted that the mounting holes 672, 674, 676, 682 and 684 of casing section 604 are positioned to be in alignment with 620, 622, 624, 630, and 632 of casing section 606 when the two halves of the casing are aligned.

Troughs 610 and 654 cooperate to define a cavity 686 (FIG. 10) that extends the length of the casing (excluding the wings) when the two halves are aligned. Also, raised detents 656, 658; 660, 662; 664, 666; and 668, 670 of casing section 606 are positioned to be aligned across from the raised detents 634, 636; 638, 640; 642, 644; and 646, 648, respectively, of casing section 604 when the two casing sections are aligned in an assembled arrangement.

Valve 600 includes a slide housing 686 that fits between the two halves of the casing. The slide housing 686 and internal slide 688 are shown in detail in FIGS. 4, 5 and 7. Slide housing 686 has a casing 690 comprising a substantially cylindrical wall 690 with a longitudinal inner bore 692.

The cylindrical wall 690 is dimensioned to seat in cavity 686. Slide housing 686 includes a series of connector nipples 694, 696, 698, 700 evenly spaced along its length. Each connector nipple has an inner bore, as at 701, which is perpendicular to, and opens into, inner bore 692. The respective connector nipples, in the embodiment illustrated, have a substantially semi-circular or D-shaped cross section. As best seen in FIG. 5, nipple connector 694, 696, 698, and 700 each has a pair of spaced apart circumferential retainer grooves 702 and 704, 706 and 708; 710 and 712, and 714 and 716, respectively, in external surface of the nipple connector.

The nipple connectors are designed to seat in the connector seats 612, 614, 616 and 618. The pairs of detents 634, 636, 638, 640, 642, 644 and 646, 648 formed on the surface of the connector seats align with the pairs of grooves on the rounded side of the connector seat when the connector nipples are positioned in the connector seats. The retainer grooves on the flatter side of the connector nipples align with the detents 656, 658; 660, 662; 664, 666; and 668, 670 on the surface of the second casing section 606 when the valve is assembled. The nipple connectors 694, 696, 698, 700 are dimensioned to fit snugly inside the ends of the air conduits 6, 8, 10 and 12, as will be explained in greater detail below.

Internal slide 688 is engaged in slide housing bore 692 so that it can move axially within the slide housing bore. Slide 688 is generally tubular in construction having a wall 689 and internal bore 720. There is a series of linearly aligned, spaced apart openings or ports 722, 724, 726 and 728 that open into bore 720. O-ring seals 730, 732, 734, 736, 738, 740, 742, 744, and 746 are position on each side of the respective ports to make a fluid or airtight seal around the ports and create discrete air chambers C-1, C-2, C-3, and C-4. Air in the chamber can flow around the circumference of the slide and enter the associated port. The slide 688 is plugged at each end with plugs 748 and 750. There is a flat washer 751 between the threaded plug and the end of the slide to facilitate sealing the end of the slide with the plugs. Plugs 748 and 750 provide structure for the user to grasp or touch to manipulate the slide and operate as stops when the slide is moved axially within the casing bore. The air chambers around openings 722, 724, 726 and 728 are placed into and out of alignment with the nipple connectors 700, 698, 696 and 694, respectively, when the nipple connectors are attached to the air conduits, to open and close the valve and to allow air flow or block air flow among the cushion A inflation zones, as explained with reference to other exemplary embodiments above.

It will be appreciated that, although in the illustrated embodiments, for purposes of clarity, the slide ports are aligned, and in registry with, the openings to the air conduits, it is not necessary that the two sets of openings be in perfect alignment. For the slide to function in an open position, for example, all that is necessary is for the air chambers C-1, C-2, C-3, and C-4 to be in alignment with the openings. As explained above, the air can flow around the slide within the air chamber and enter or exit through the port. This allows the slide valve to function even if the user inadvertently rotates the slide around its longitudinal axis, taking the two sets of openings out of registry. Thus, when reference is made to the slide ports and the openings to the air conduits being in alignment or registry, this generally is defined as the air chambers around the slide ports being appropriately positioned with regard to the openings to the air conduits so as to allow fluid communication through the slide ports and the air conduits. Hence, it is not necessary that the two sets of openings be in perfect alignment or registry, but only requires functional alignment, that is, an alignment that allows the fluid flow function between the conduit opening and the associated slide port.

The outer casing, slide housing, and slide can be cylindrical, ovoid, triangular, and rectangular or any other shape in cross-section as long the slide can be manipulated from side-to-side to move the respective openings into and out of functional alignment.

Figure 10:
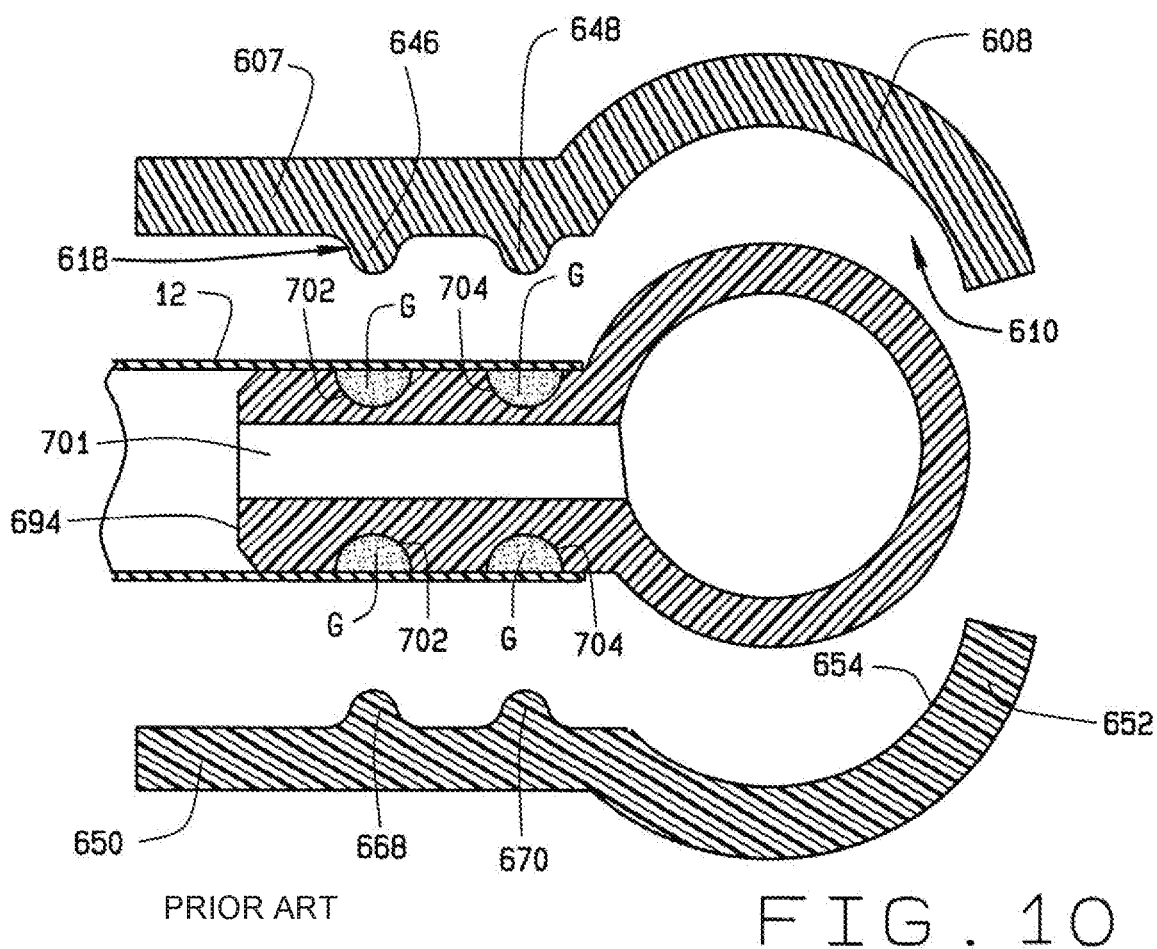
Figure 11:
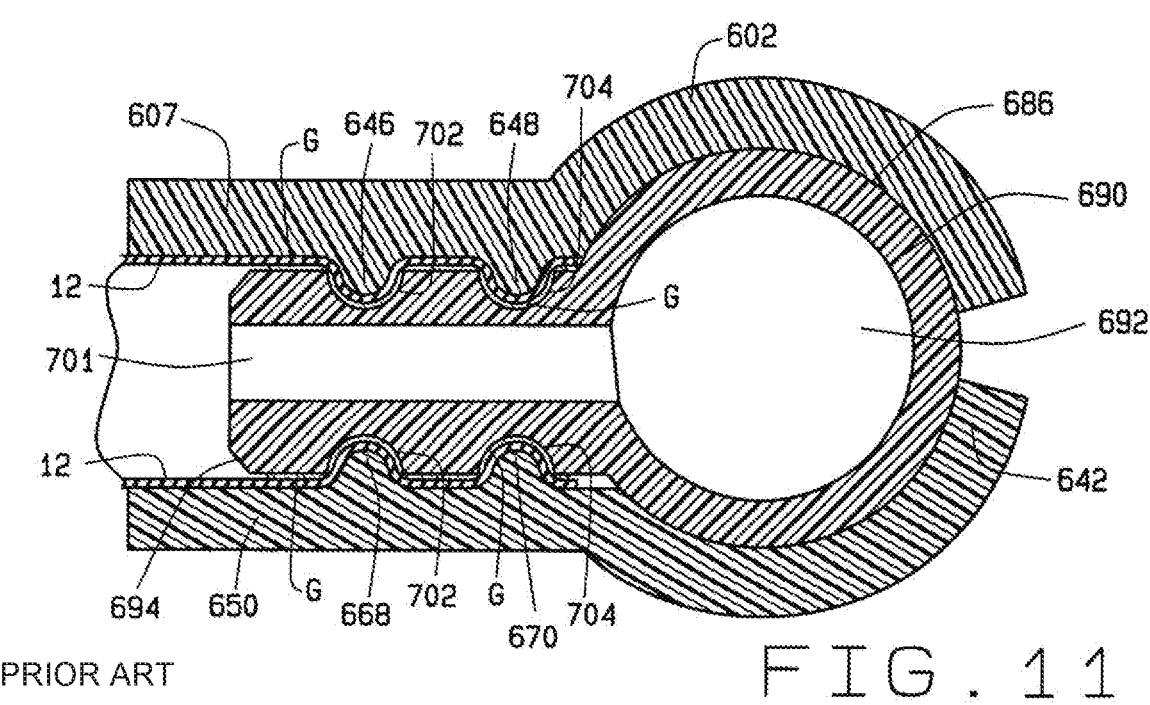

The structure of valve 600 provides for enhanced attachment to cushion A, as will now be explained. Referring now to FIGS. 3, 10 and 11, it will be understood that one each of the nipple connectors is introduced into the open end of one of the air conduits. In the embodiment shown, each conduit has a generally D-shaped cross section, raised on the top side and flat on the base side. By way of example, referring to FIGS. 10 and 11, nipple connector 694 is inserted into the end of air conduit 12. Once the connector nipples are positioned in an air conduit, the two halves 606, 608 of the valve casing are positioned on each side of the slide housing 686 in a clamshell arrangement with the slide housing body 690 seated in cavity 686. The relatively flat forward sections of the casing halves, 607 and 650 overlap peripheral edge E of the cushion. The two halves then are tightly fastened together with rivets, or other appropriate fasteners such as screws or the like, through the opposed and aligned mounting holes 672, 674, 676, 682, 684 and 620, 622, 624, 630 and 632 and through holes punched in the peripheral edge of the cushion A. As illustrated, peripheral edge E and air conduit 12 are impinged between the casing halves, in particular, pinching the material between the retainer grooves 702, 704 and the opposed detents 646, 648 and 668, 670. This impinging arrangement exists along the length of the valve, including each air conduit, thereby tightly clamping the valve to the periphery of the cushion A to prevent the valve from pulling out of the cushion.

Furthermore, as shown in FIG. 10, prior to insertion of a nipple connector into the conduit, adhesive or glue G can be introduced into the retainer grooves, as illustrated, grooves 702 and 704. Because a dollop of the adhesive is applied in the grooves, when the nipple connector is inserted into the open end of the conduit, the glue G generally stays in place in the grooves and is not mechanically pushed toward the body of the slide housing by the conduit wall, as can happen if adhesive is applied to a connector nipple having a smooth surface. When the two halves of the valve are tightened together, the detents engage the retainer grooves and force the adhesive out of the retainer grooves, causing it to flow onto the surfaces along the length of the nipple connector and the air conduit, as shown in FIG. 10, to provide for a better bond between the nipple connector and the air conduit. This process, of course, is duplicated with each nipple connector and air conduit. Consequently, the valve of the present invention provides for an enhanced mechanical attachment and adhesive attachment to the cushion.

Although valve 600 as illustrated provides for two retainer grooves on each connector nipple and, correspondingly, two retainer detents on the inside surfaces of both the first casing section and second casing section, it will be understood that various aspects of the invention can be accomplished if the nipple connector had one or more than two retainer grooves. Correspondingly, the casing halves can have one retainer detent or more that two. It is within the scope of the invention if the nipple connector has more retainer grooves than the casing sections have detents. Valve 600 can be constructed with more than four connector nipples or fewer than four connector nipples if there are more or less air conduits on the inflatable cushion.

As explained above with reference to other exemplary embodiments, an inflation apparatus also could be attached to valve 600 to allow inflation of all four zones of the cushion as described in detail above. As with the other embodiments, valve 600 can have an appropriate detent structure associated with the slide or the slide housing to secure the slide in place.

Figure 12:
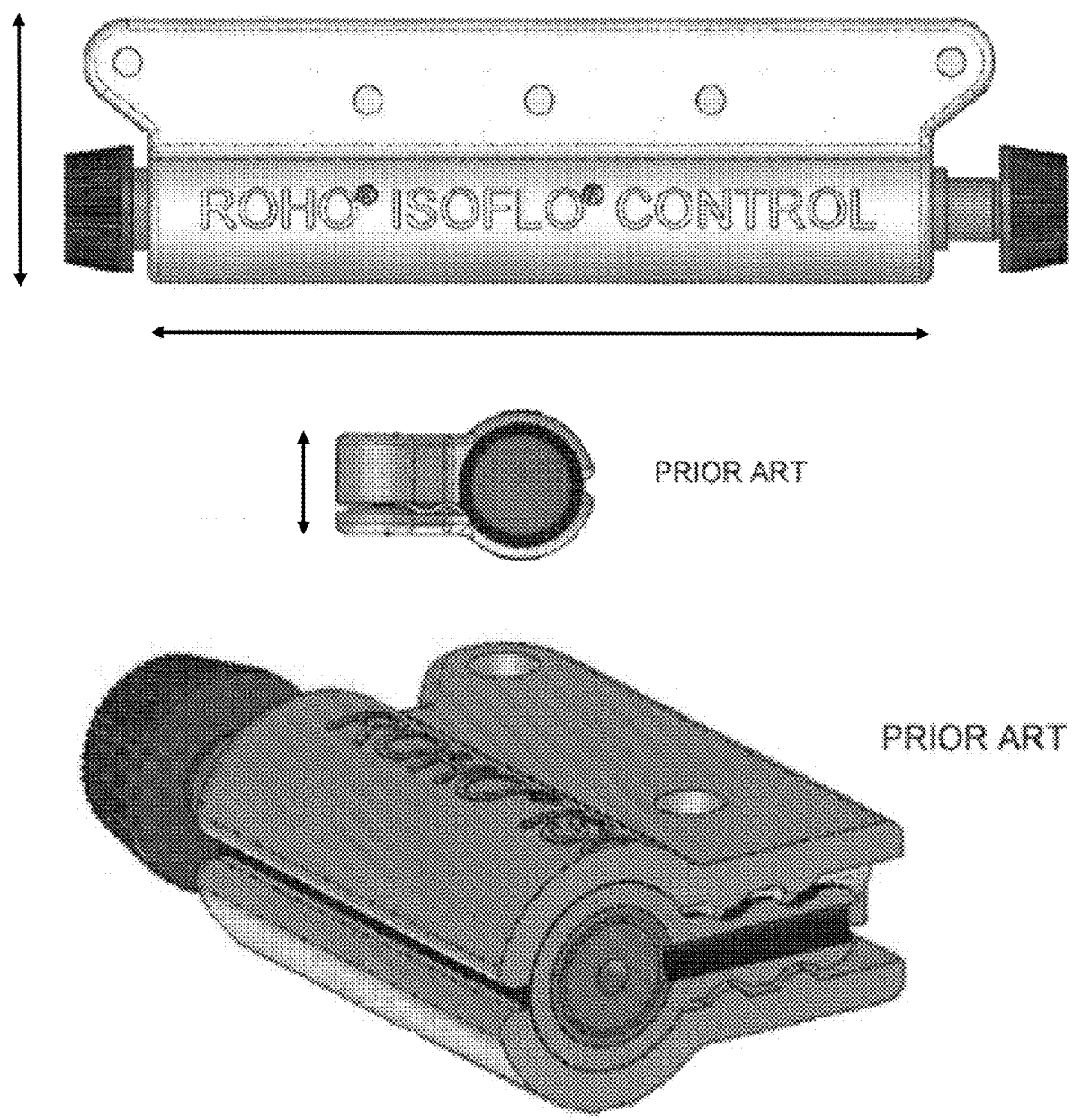

FIG. 12 provides a top view, side view, and isometric projection of one embodiment of the valve assembly 600. The dimensions shown in FIG. 12 are provided by way of example only, and are not intended to limit the size or scale of the existing valve assembly 600 or the presently disclosed manifold valve assembly 100.

Referring now to FIGS. 13-23, the manifold valve assembly of the present disclosure is a new apparatus that offers a number of improvements over the existing valve assembly 600. Although similar to the existing valve assembly 600 with regards to the general principals of operation, the manifold valve assembly 100 further includes one or more pressure sensors, communication devices, associated electrical components including lights or other visual indicators, and a power source to allow remote access and evaluation of the pressure values of the zoned cellular cushions. FIGS. 13-17 depict an embodiment of the manifold valve assembly 100 engaged to a portion of a cellular cushion 1 that includes exemplary inflation cells 4.

Figure 13:
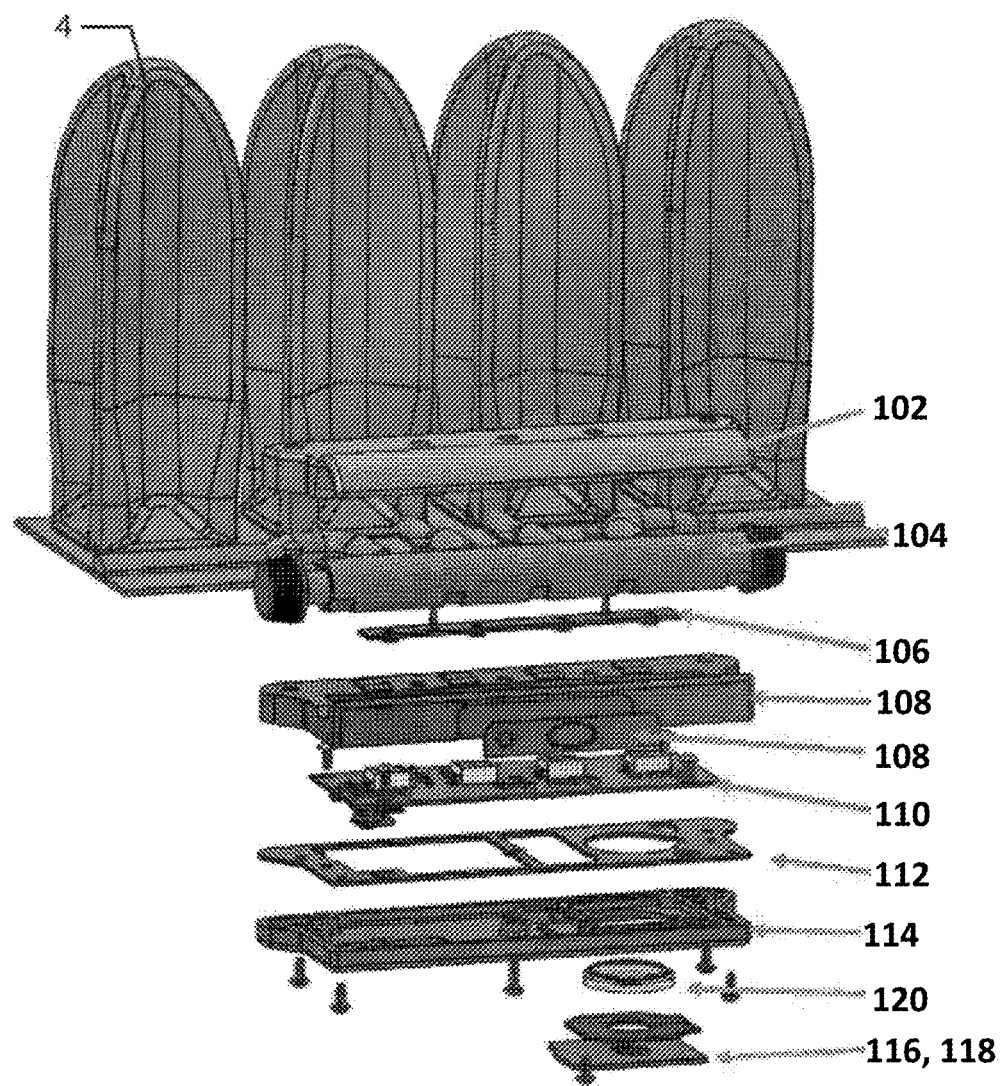
FIG. 13 is an exploded view of a manifold valve assembly for zoned cellular cushions according to one embodiment.
Figure 14:
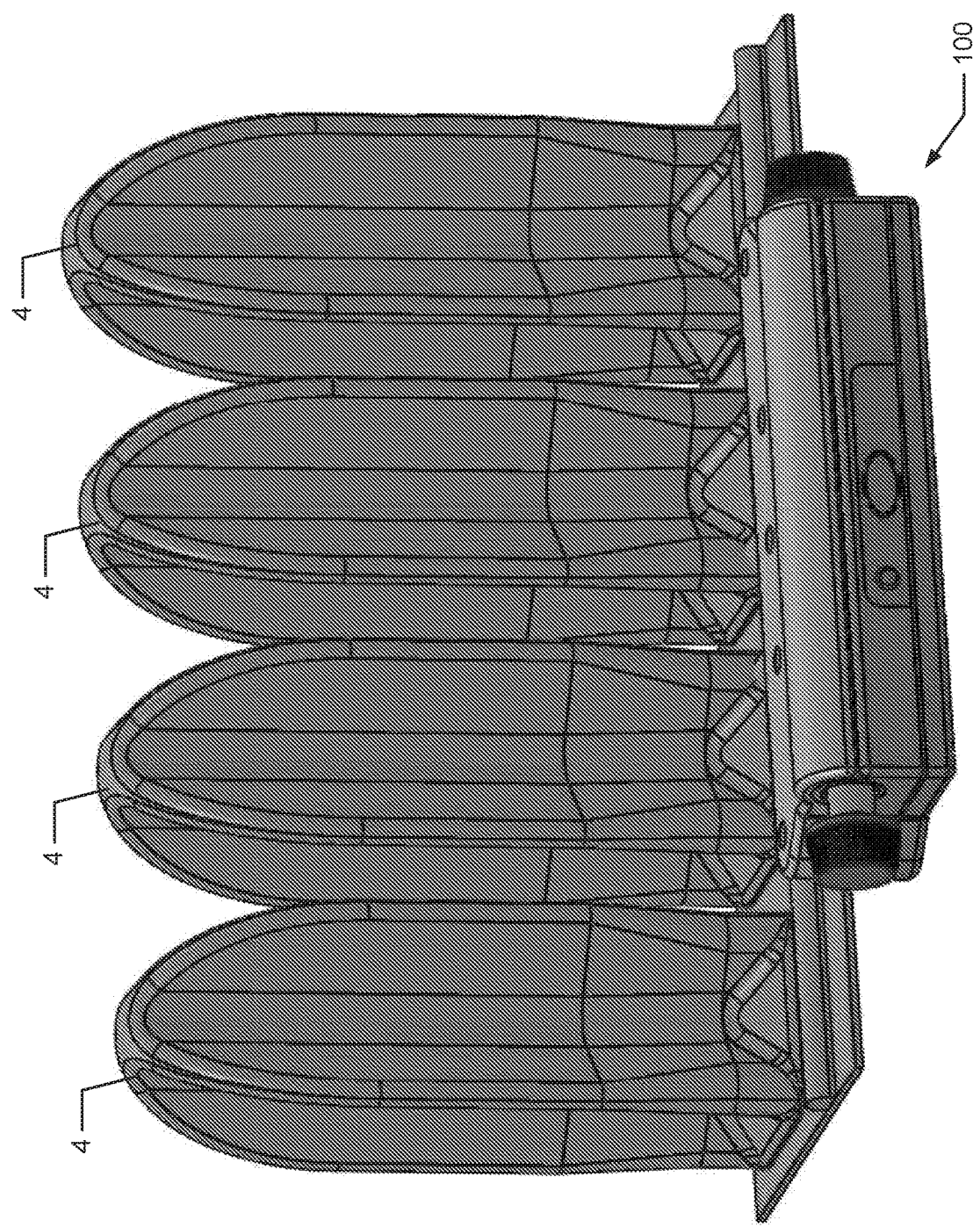
FIGS. 14-17 are views of the manifold valve assembly for zoned cellular cushions in an assembled configuration according to one embodiment.

FIG. 13 is an exploded view of the embodiment of the manifold valve assembly 100. The manifold valve assembly 100 includes a top cover 102, the slide housing 104, the transducer gasket 106, a bottom cover 108, a printed circuit board (PCB) 110 including one or more transducers, processors, and transceivers, an enclosure gasket 112, the electronics cover 114, and a the power source 120.

In one aspect, an electronic enclosure 136 is defined by the bottom cover 108 and the electronics cover 114. In another aspect, the electronics cover 114 further includes an access door 116 and associated door gasket 118 to permit access to the power source 120. In another aspect, the slide housing further includes at least the slide bore, knobs, and sealing O-rings. The slide housing may further include any additional structures and components necessary for the proper operation of the valve, as described herein or in the related patents and patent applications that have been incorporated by reference herein.

Figure 17:
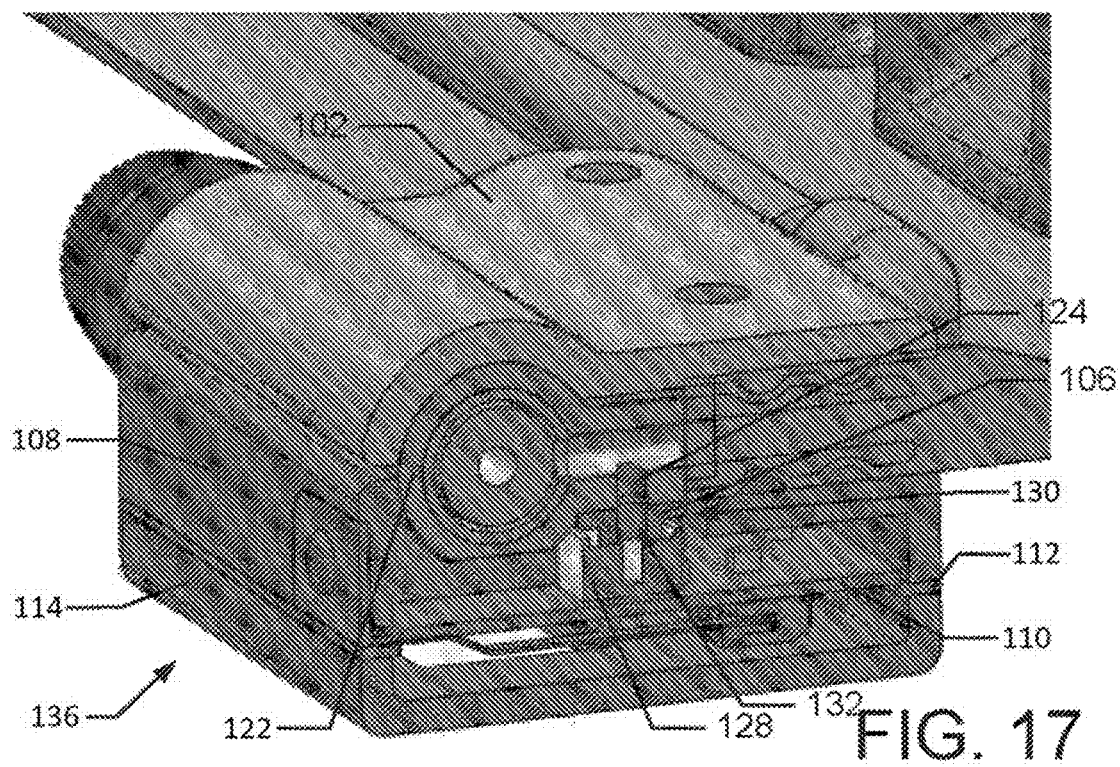

According to one embodiment, as shown in FIGS. 17 and 20, the connector nipple 122 further includes a connector nipple sensor conduit 124 formed through the sidewall of the connector nipple. The connector nipple sensor conduit 124 provides fluid communication to the interior void or bore 126 of the connector nipple. As such, a pressure transducer 128 also in fluid communication with the connector nipple sensor conduit 124 may measure the pressure within the connector nipple and therefore measure the pressure within the associated inflation zones, substantially similar to zones R, S, T, and U.

Figure 15:
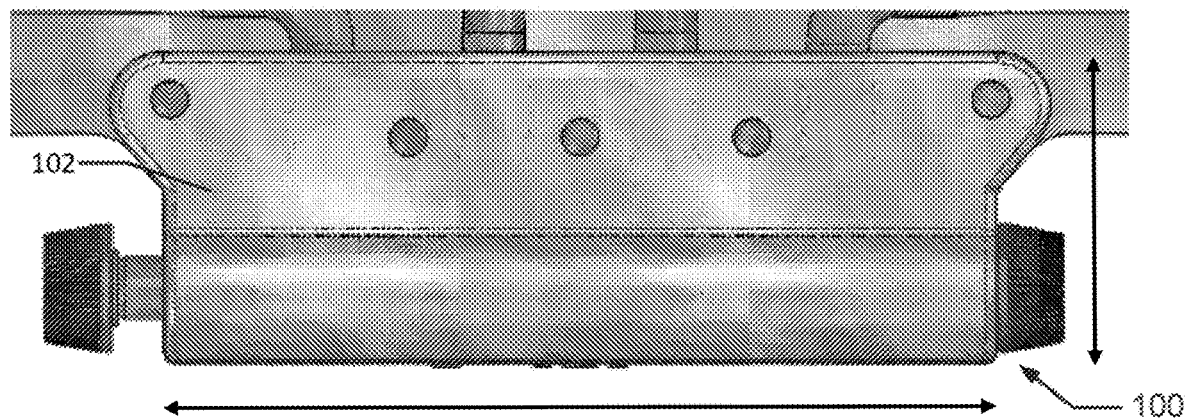
Figure 16:
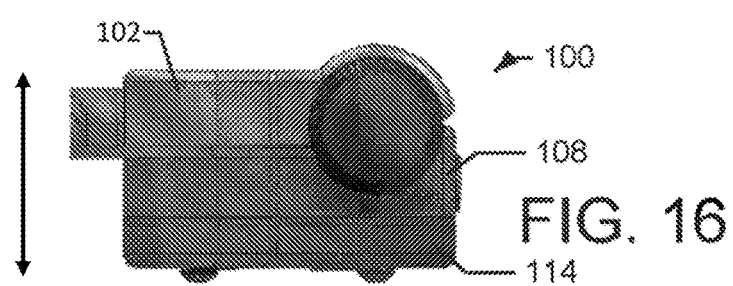

FIGS. 15 and 16 provide a top view and side view, respectively, of one embodiment of the manifold valve assembly 100. The dimensions shown in FIGS. 15 and 16 are provided by way of example only, and are not intended to limit the size or scale of the existing valve assembly 600 or the presently disclosed manifold valve assembly 100. FIG. 17 is a partial-sectional view of an assembled manifold valve assembly 100 as engaged to an embodiment of the cushion. As shown, the bottom cover 108 defines a gasket aperture 130 to receive the transducer gasket 106 that forms an air-tight seal between the connector nipple sensor conduit 124 and the pressure transducer 128. As shown the transducer gasket 106 further defines one or more gasket conduits 132 that are in fluid communication with both the connector nipple sensor conduit 124 and the transducer 128, when the manifold valve assembly 100 is assembled. In one embodiment, the manifold valve assembly 100 includes a plurality of transducer gaskets 106, where each gasket defines a single gasket conduit 132 that corresponds to a single connector nipple 122. In another embodiment, the manifold valve assembly 100 includes one or more elongated transducer gasket 106, where each elongated gasket defines a plurality of more gasket conduits 132, where the number of gasket conduits corresponds to the number of connector nipples 122.

The pressure transducer 128 is engaged to and in electrical communication with the PCB 110 that is in further electrical communication with the power source 120 and a communication device 134. The PCB 110 is mounted within the electronics enclosure 136 using any suitable means as understood by one having ordinary skill. As shown in FIG. 17, the electronics enclosure 136 also includes one or more enclosure gasket 112 to seal and maintain a sealed water resistant environment within the manifold valve assembly 100. As shown in FIG. 17, the electronic enclosure is defined by the bottom cover 108 and the electronics cover 114.

FIG. 18 is a front elevation view of one embodiment of the slide housing 104, with the connector nipples 122 projecting therefrom. The slide housing 104 is shown without the slide or plugs, as shown and described in the related '936 patent. In one aspect, the slide housing 104 may be a molded component having a unitary construct. In another aspect, the slide housing 104 may be formed from one or more components engaged to one another.

FIG. 19 is a view of the bottom of the slide housing 104, while FIG. 20 is a cross-sectional view of the slide housing as viewed along line A-A. As shown, the bottom of the slide housing 104 includes a number of pressure conduits 138 that are aligned and in fluid communication with the connector nipple sensor conduit 124 of each connector nipple 122. The bottom of the housing 104 also defines one or more fastener openings 140 for engaging the slide housing 104 to the bottom cover 108. FIG. 21 is an orthographic side view of the embodiment of the slide housing 104 as shown in FIGS. 18 and 19. Similarly, FIG. 22 is a partial cross-sectional view of the bottom of the slide housing 104 as viewed along line B-B of FIG. 21.

FIGS. 23A-C are orthographic views of one embodiment of the electronics cover 114 with the PCB 110 and power source 120 disposed therein. FIG. 23A is a top plan view of the PCB 110 with one or more pressure transducers 128 mounted thereon. Preferably, the number of transducers 128 corresponds to the number of inflation zones in the cushion 1. Preferably, the portion of the electronics enclosure containing the transducers 128 is a water-tight environment. As such, the electronics cover includes one or more gasket 112. The PCB 110 may be fixedly or, alternately, removably engaged to the electronics cover 114 using screws or any other suitable fasteners 142.

Figure 23D:
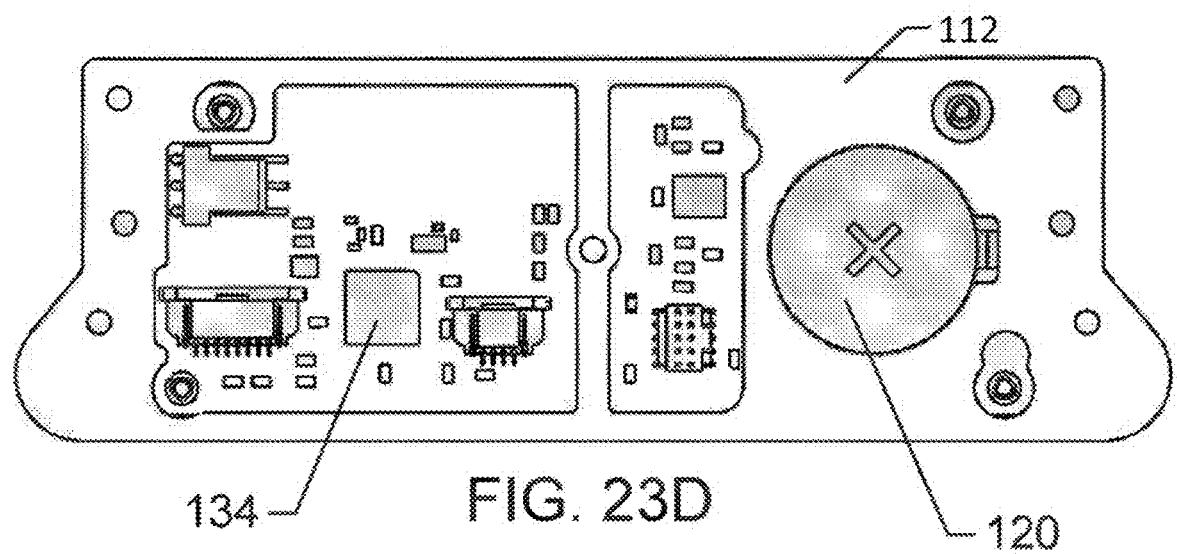
Figure 23E:
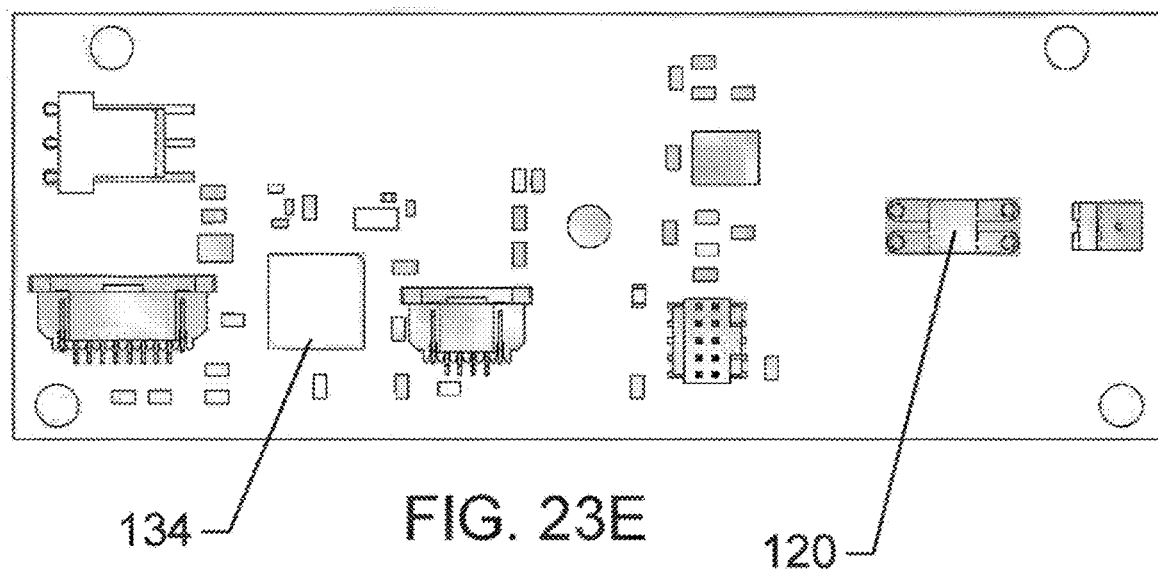

FIG. 23B is a bottom plan view of the electronics cover 114, while FIG. 23C is a side elevation view of the electronics cover 114 and PCB 110. For illustration purposes only, the bottom of the enclosure cover 114 is shown without any access doors or door gaskets. In one aspect, the power source 120, such as a battery, is mounted on the PCB 110 opposite the transducers 128. Similarly, the communication device or transceiver 134, such as a Bluetooth low energy device (BLE), is also mounted on the PCB 110, as shown in FIG. 23D-E. FIG. 23D shows the PCB 110 with the gasket 112, while 23E shows an embodiment of the PCB 110 that has not been mounted in the electronics cover 114 with the another embodiment of a battery 120. Although, the power source 120 and transceiver 134 are shown isolated from the transducers, one of ordinary skill may arrange the components of the PCB 110 in any suitable manner.

An embodiment of the manifold valve assembly 100 shown in FIGS. 13-23 includes transducers and other electronic components engaged to a bottom portion of the valve assembly. In contrast, another embodiment of the manifold valve assembly 200 is shown in FIGS. 24A-26C. This embodiment provides a more compact design, where the transducers and other electronic components are removably engaged to a rear-facing portion of the valve assembly.

FIGS. 24A-B, 25A-B, and 26A-B provide top plan views and a rear elevation views of another embodiment of the valve assembly 200 engaged to a cushion 1. For purposes of illustration only, the air cells 4 have been omitted from the figures for clarity.

Figure 24A:
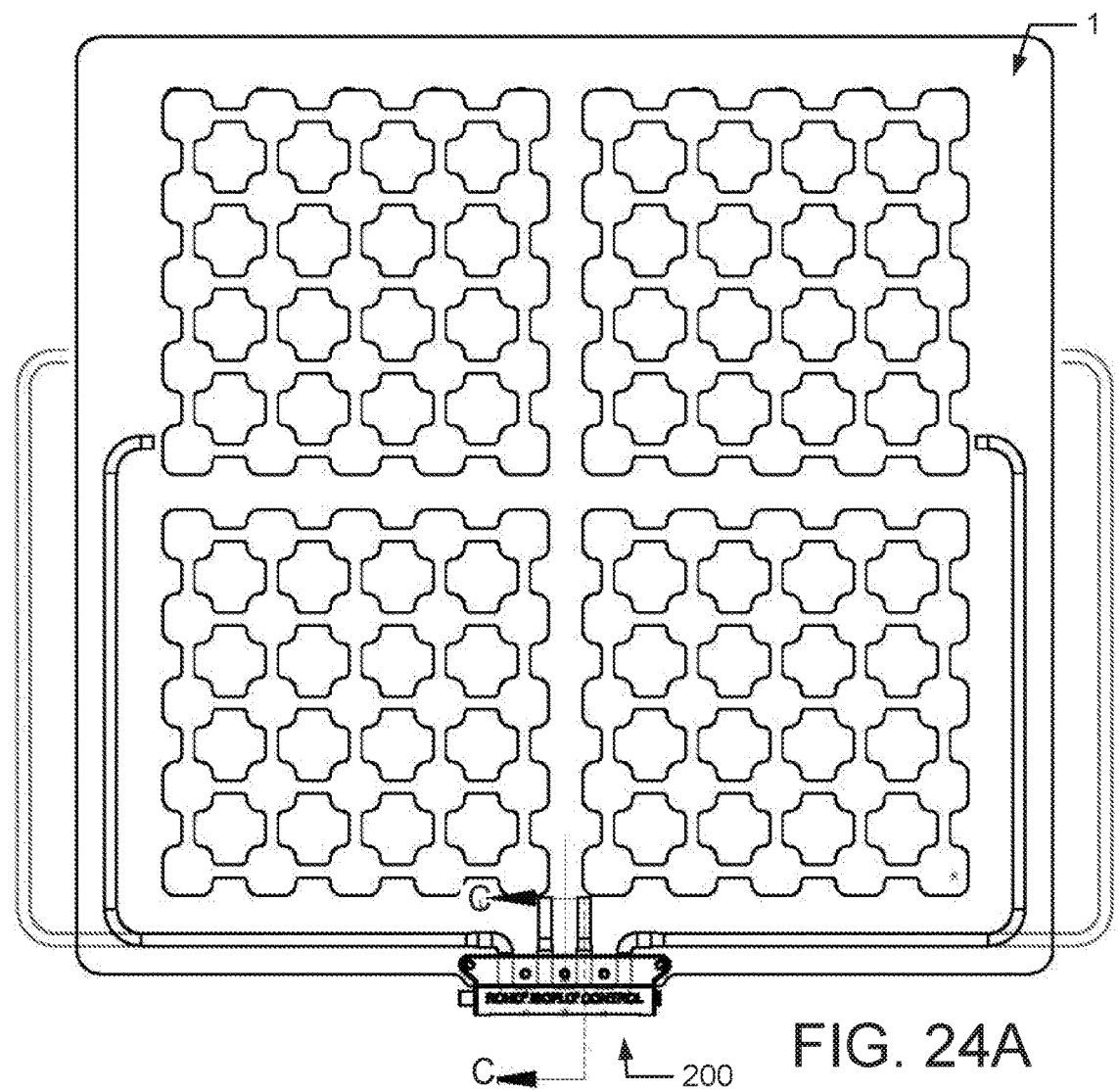
FIGS. 24A-C are views of another manifold valve assembly for zoned cellular cushions without engaged electronic components according to one embodiment.
Figure 24B:
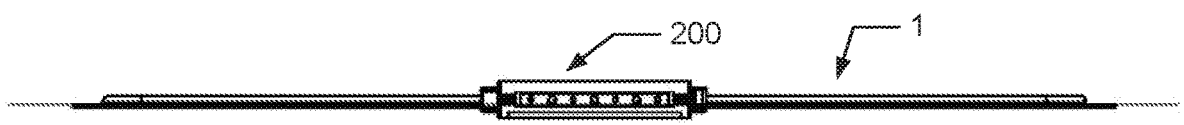
Figure 24C:
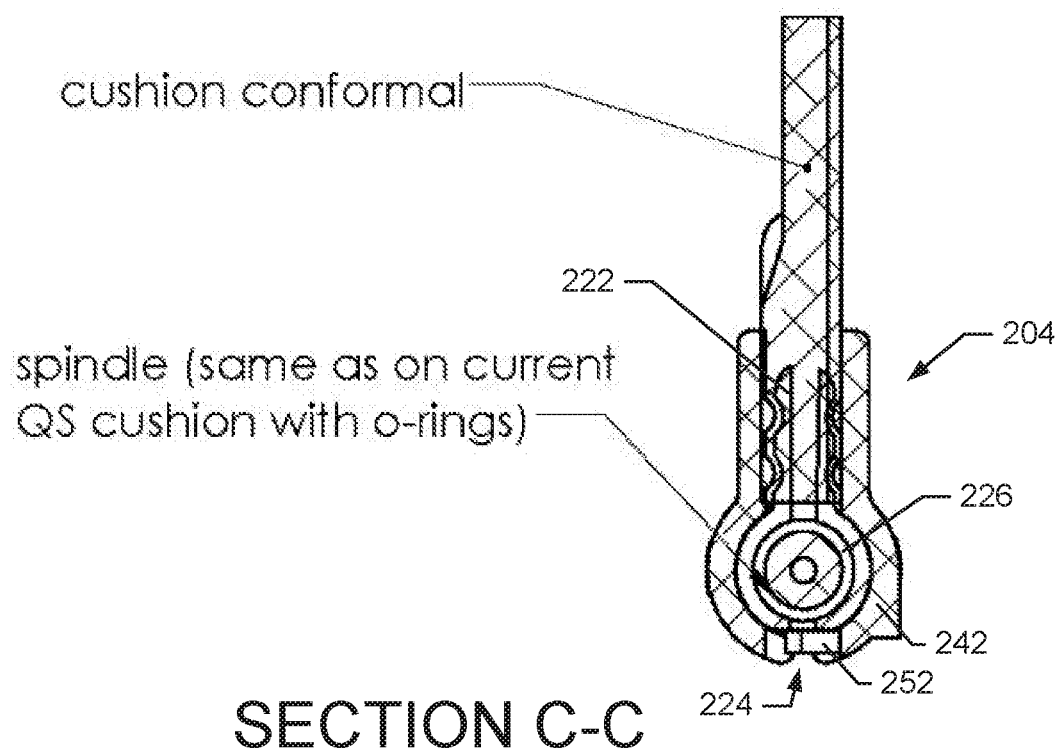

FIGS. 24A-C provide views of the manifold valve assembly 200 without any sensors or electronics. In various aspects, this sub-assembly can become either style with or without electronics. FIG. 24C is a cross-section view of the valve assembly 200 slide housing 204, including at least one connector nipple 222, as viewed along line C-C of FIG. 24A. As shown, the connector nipple pressure conduit 224 is formed in the cylindrical sidewall 242 of the housing 204. In one aspect, the slide housing 204 also includes one or more housing gasket 252 that is operatively engaged and associate with each connector nipple pressure conduit 224. As such, the connector nipple pressure conduit 224 may be covered even in the absence of a removable cover such as the electronics cover 214 or an enclosure cover 250.

According to various aspects of the present disclosure, the cushion sub-assembly shown in FIGS. 24 A and B can be manufactured to permanently include a particular embodiment of the manifold valve assembly, such as those disclosed herein (e.g. with electronics or without electronics). In other aspect, the cushion sub assembly may be manufactured as a convertible configuration, wherein the cushion may be converted from one having electronics incorporated into the manifold valve assembly to a cushion without electronics. In one aspect, the cushion sub-assembly is configured as a convertible cushion assembly or one having a permanent manifold valve configuration (with or without electronics) at the factory as part of the manufacturing process. Alternately, the cushion may be modified or reconfigured by qualified technician after manufacturing or even after sale to the consumer. As such, the cushion may be upgradeable after sale by a qualified technician.

Figure 25A:
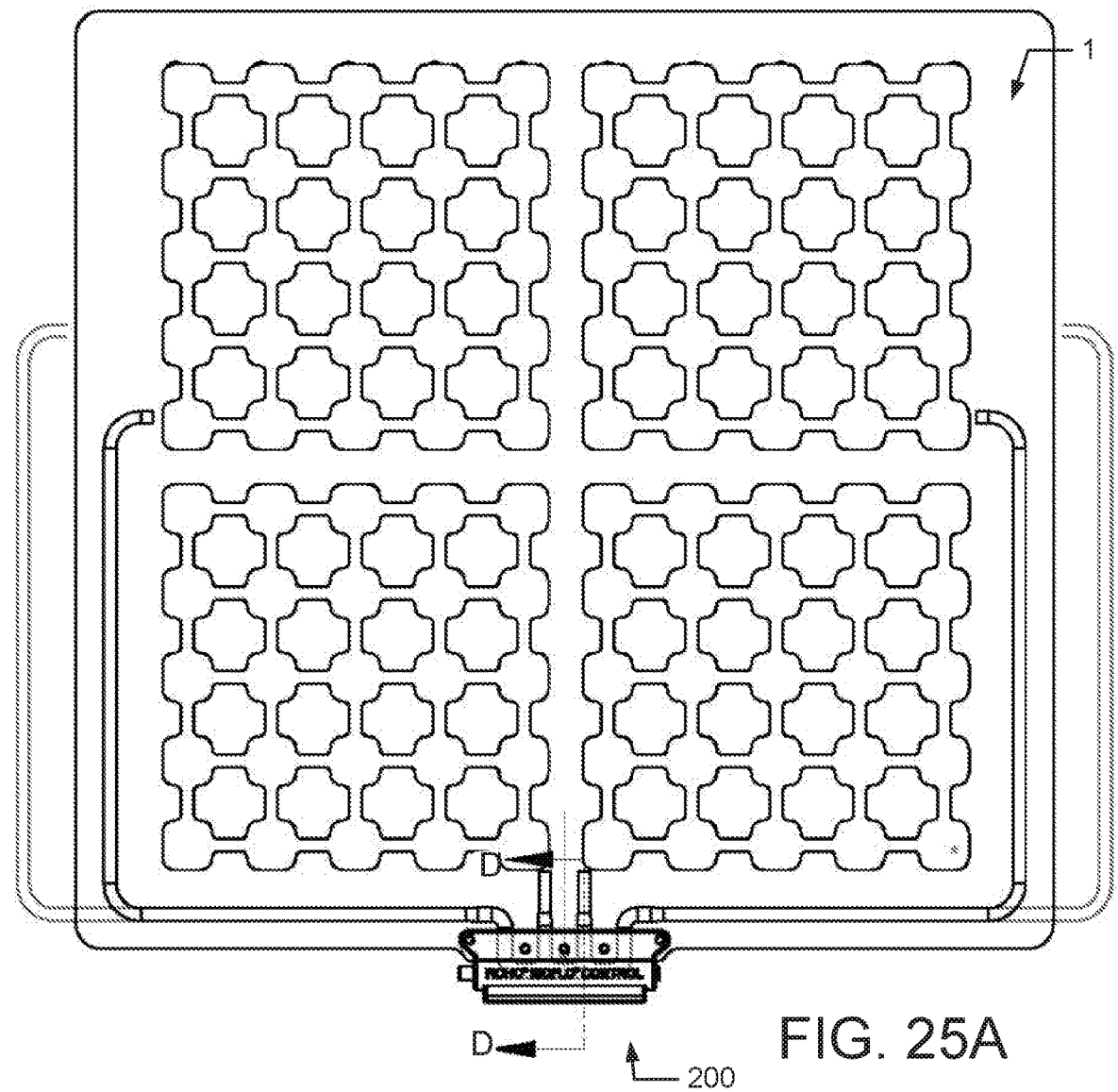
Figure 25B:
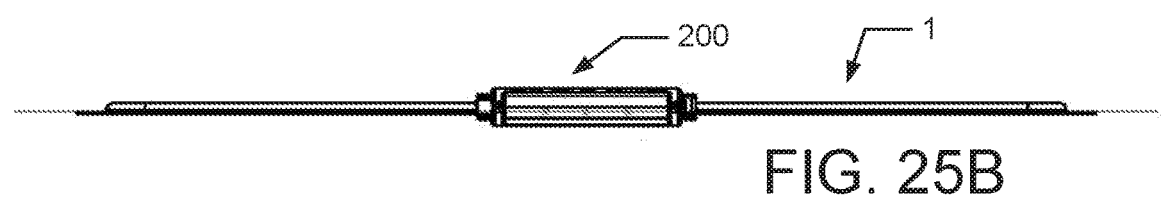

FIGS. 25A-B provide a top plan view and a rear elevation view of the valve assembly 200 with another embodiment of the electronic enclosure 236 engaged thereto. Referring now to FIG. 25C, a cross-section view of the valve assembly 200 slide housing 204 is shown, as view along line D-D of FIG. 25A. As shown, the electronics enclosure 236 includes a one or more pressure transducers 228 in fluid communication with the connector nipple pressure conduit 224 formed in the sidewall 242. The electronics enclosure 236 further includes the transducer gasket 206, the PCB 210, and electronics cover 214. The electronics enclosure 236 also includes the power source 220, shown in FIG. 25D, and a transceiver (not shown). In one embodiment, the power source 220 and transceiver may be housed beneath the valve assembly 200, without substantially increasing the thickness of the assembly. Alternately, in another embodiment, the power source and transceiver may be disposed anywhere along the length of the enclosure 236. In yet another embodiment, the power source 220 and transceiver are positioned at either lateral end of the enclosure 236 or both. As shown in FIG. 25C, the electronic enclosure 236 is defined by the slide housing 204 and the electronics cover 214.

Figure 26A:
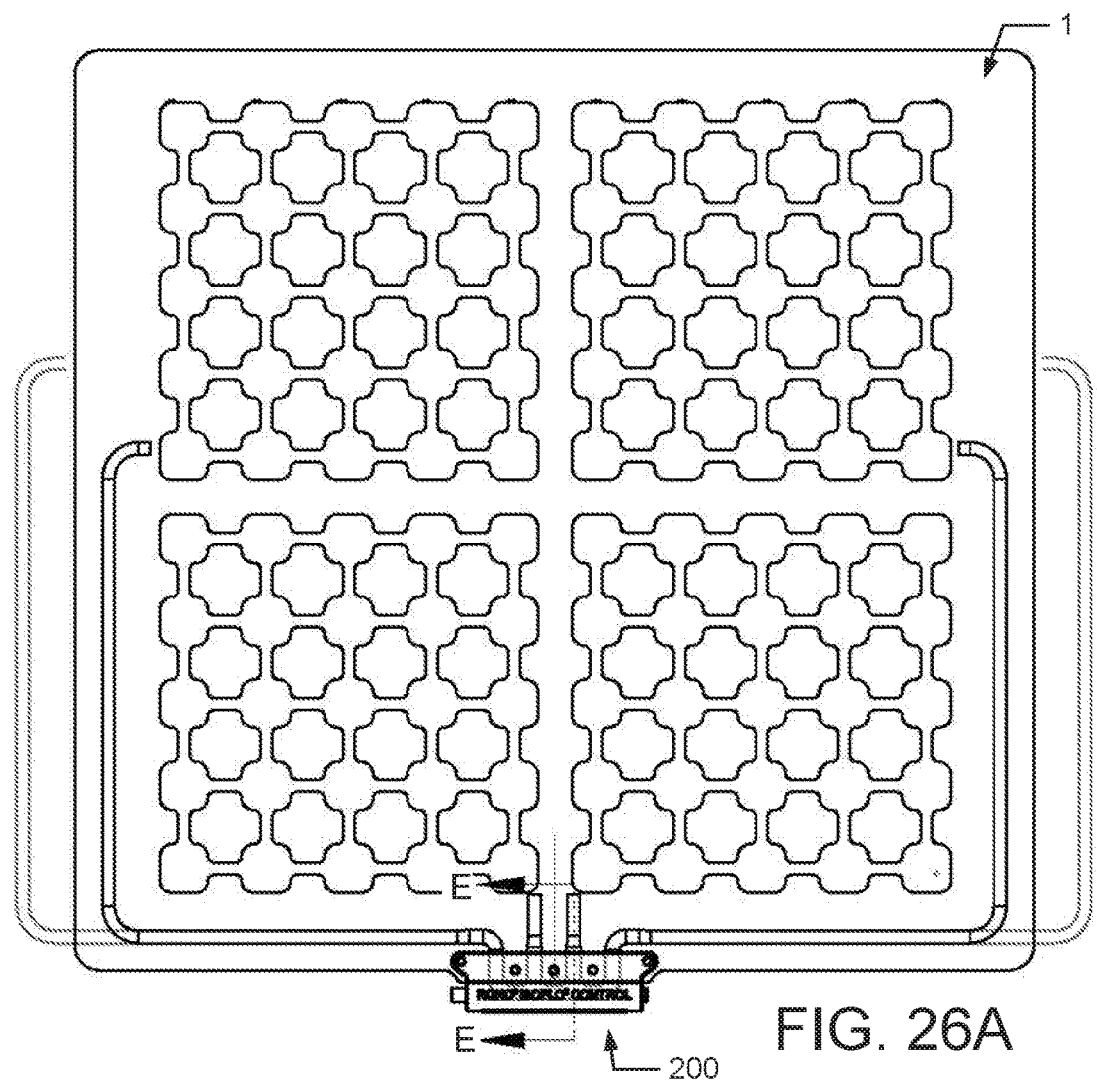
FIGS. 26A-C are views of another manifold valve assembly for zoned cellular cushions in a maintenance configuration according to one embodiment.
Figure 26B:
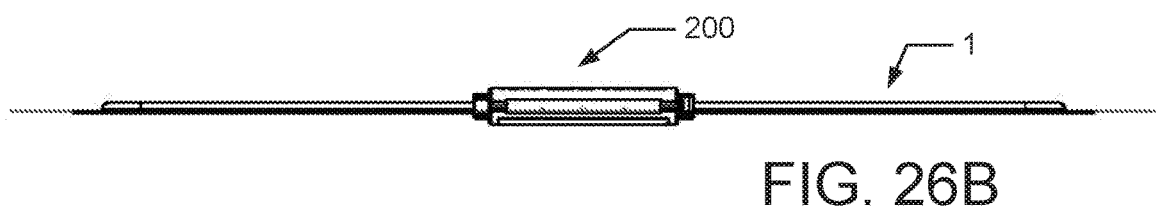
Figure 26C:
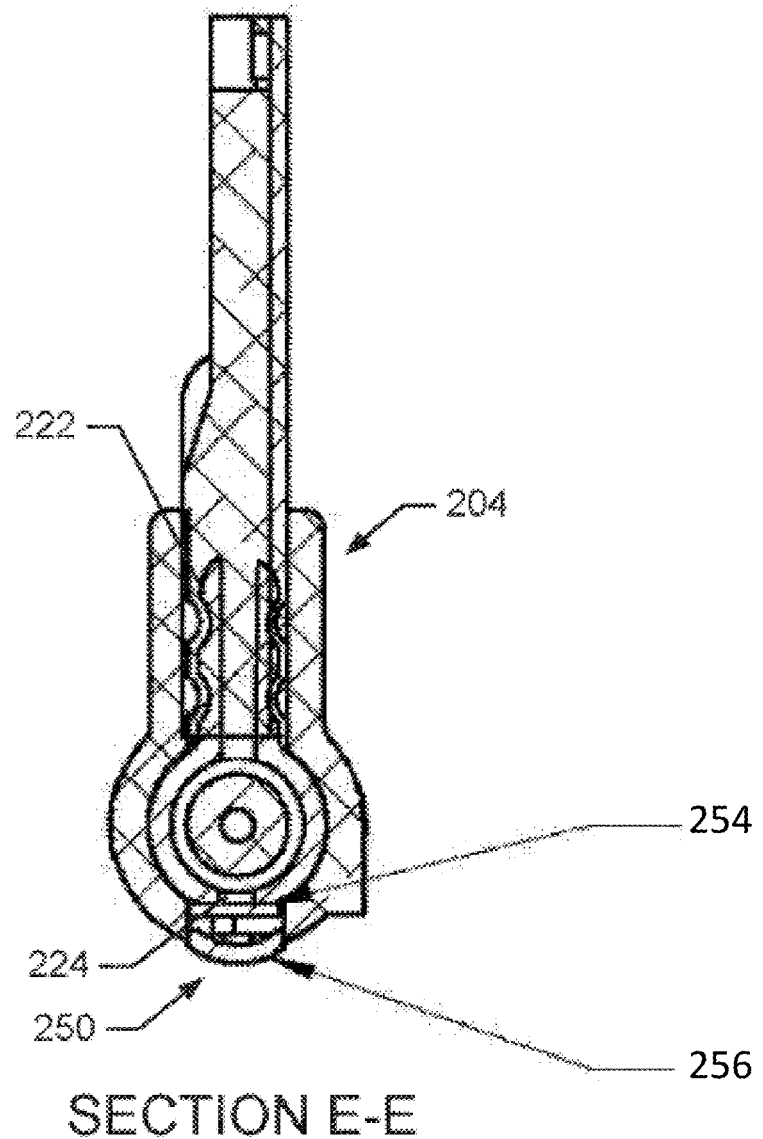

FIGS. 26A-B provide a top plan view and a rear elevation view of the valve assembly 200 with an enclosure 250 engaged thereto. Referring now to FIG. 26C, a cross-section view of the valve assembly 200 slide housing 204 is shown, as view along line E-E of FIG. 26A. As shown, the enclosure 250 includes a sealing gasket 254 and maintenance cover 256. When engaged to the manifold valve assembly 100, the maintenance enclosure 250 provides an airtight seal to the assembly such that the cushion 1 remains inflated. Alternatively, the enclosure 250 seals the manifold valve assembly 100 and cushion air conduits, such as, air conduits 6, 8, 10 and 12 should the cushion require cleaning.

Figure 27:
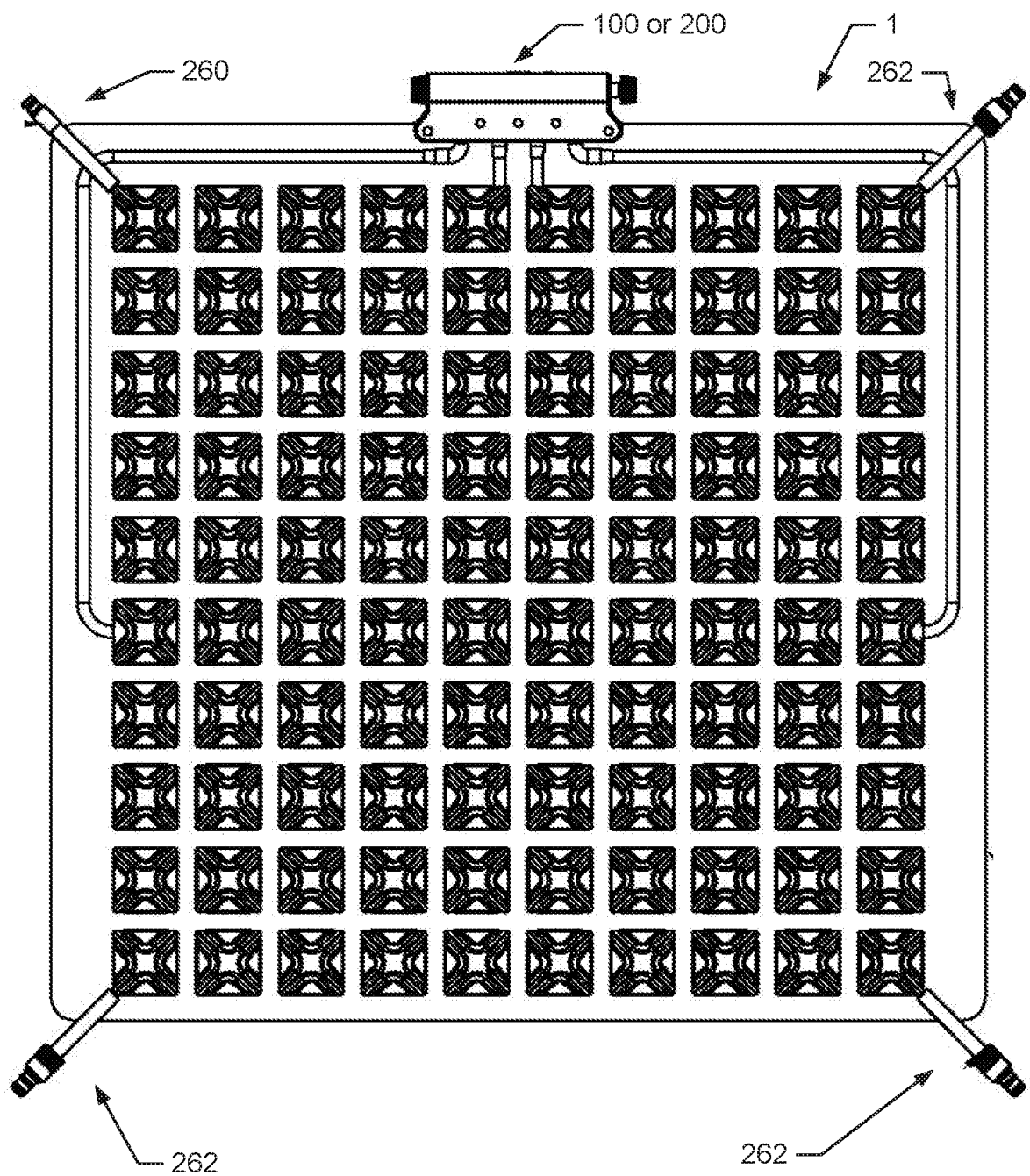
FIG. 27 is a plan view of an embodiment of a zoned cellular cushion for use with the at least one embodiment of the manifold valve assembly.
Figure 28:
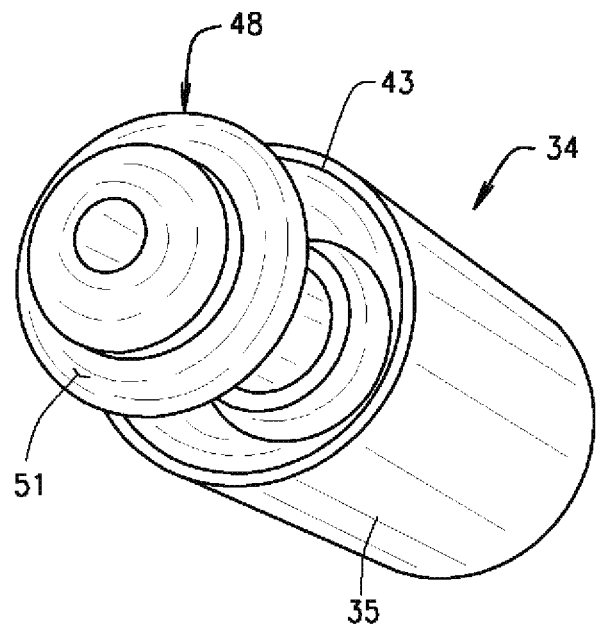
FIG. 28 is a proximal end perspective view of one aspect of a reduced outflow valve.
Figure 29:
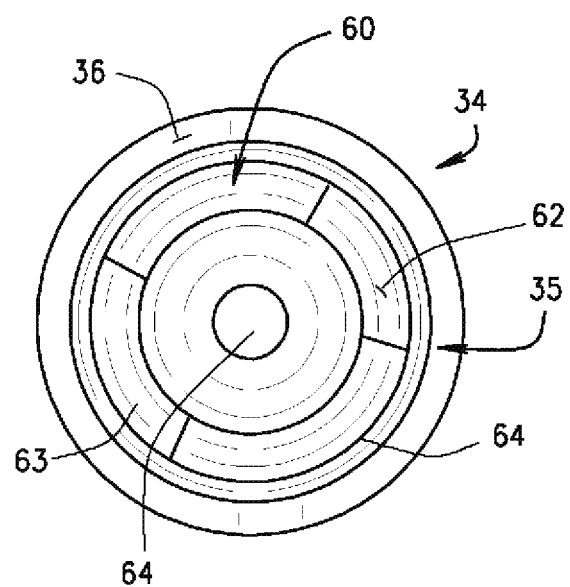
FIG. 29 is a proximal end perspective view of the reduced outflow valve of FIG. 5.

FIG. 27 is top plan view of one embodiment of a cushion 1 operatively engaged to a manifold valve assembly 100 or 200. As shown, various embodiments of the cushion 1 may also include one or more bleed valve and hose assembly 260, such as that disclosed in international PCT application No. PCT/US2014/066182, entitled "Reduced Outflow Inflation Valve," filed on Nov. 18, 2014, and published on Aug. 6, 2015 as WO 2015/116305 A1, ("the '182 Application"), which is incorporated herein by reference in its entirety. The cushion 1 may also include a quick-connect hose assembly 262 for use with an external immersion sensor (not shown) such as the disclosed in International PCT patent application No. PCT/US2014/066181, entitled "Cushion Immersion Sensor," filed on Nov. 18, 2014, and published on Aug. 6, 2015 as WO 2015/116304, which is also incorporated herein by reference in its entirety.

Various embodiments of the cushion 1 used with the manifold valve assembly 100, may include a reduced outflow valve 20, such as the various embodiments described and disclosed in the '182 Application. Example embodiments are shown in FIGS. 28-35. The reduced out-flow valve is typically disposed in one or more of the hose assemblies 262 that facilitate the controlled inflation and release or bleeding of air from one or more of the cushion zones. One embodiment of a reduced outflow valve 20 is shown in FIGS. 28-31. Valve 20 has a valve body 35 comprising cylindrical wall 36 which has a substantially uniform thickness along its longitudinal dimension. Viall 36 is sized and dimensioned to fit within inflation tube 6 with a snug friction fit. Cylindrical wall 36 defines an inner bore 39. There is an internal circumferential shoulder 40 at a first end of the body. Shoulder 40 defines a circular opening 42 which is in communication with bore 39. There is a tapered counter bore 43 in the first end of the body in communication with opening 42. The opposite or second end of body 35 defines a circular opening 46. As shown, opening 42 is smaller in diameter than opening 46.

A plunger 48 is slidingly engaged within bore 39 such that it can slide or move back and forth longitudinally within bore 39. Plunger 48, which may also be referred to as a piston, a slide, a baffle or the like, has an elongated body 50 with a flange 51 at a first or distal end comprising a first circumferential shoulder 52 and a second spaced apart circumferential shoulder 54 adjacent the first shoulder. The juncture of these two circumferential shoulders defines seat 56 for an O-ring seal 58. O-ring 58 is dimensioned to fit within counter bore 43 when plunger 48 slides toward the second end of body 35 within bore 39. There is a stop 59 comprised pair of opposed arcuate shoulders 60, 61 at the extreme proximal end of the plunger. Shoulder 60 and 61 define air flow spaces 62, 63 between them. The radial expanse of shoulders 60 and 61 is greater than the diameter of circumferential shoulder 40 inside wall 36. Plunger 48 defines an inner bore 64 that extends the entire length of the plunger. Bore 64 is a substantially uniform diameter along its longitudinal expanse and relatively small in diameter.

As best seen in FIG. 30, valve 20 is dimensioned to fit snugly within the bore 66 of inflation tube 6. As shown, inflation valve 8 with an associated stepped fitting 67 is inserted into the open end of the inflation tube and held securely in place. However, any method or apparatus for attaching an inflation valve to the tube is appropriate. Valve 20 is orientated within bore 66 of the tube such that opening 46 is orientated toward inflation valve 8. When air is introduced through valve 8 to inflate the cushion, for example by a pump, the force of the pump air urges plunger 48 axially within bore 39 to a first position where shoulders 60 and 61 of stop 59 abut shoulder 40 as seen in FIG. 31. The air is pumped through air flow spaces 62 and 63 and through plunger bore 64 relatively unimpeded.

However, when the cushion is overinflated and the user opens valve 8 to release air from the cushion, the force of the air toward valve 8 forces plunger 48 to move axially in bore 39 to a second position where O-ring 58 seats in counter bore 43 to effectively block air flow through the bleeder valve except for flow through plunger bore 64. Although the O-ring/shoulder/counter bore arrangement works well for its intended purpose, any element that effectively stops axial movement of plunger 48 in bore 39 will suffice. Air flow out of the cushion is impeded or dampened, which helps prevent rapid deflation of the cushion. Hence, valve 20 allows for more rapid inflation of the cushion and slower deflation of the cushion.

Another aspect of a reduced outflow valve is indicated generally by number 70 in FIGS. 32 through 35. It should be noted valve 70 comprises only two parts. Valve 70 has a cylindrical body 72 comprising a cylindrical wall 73 defining a longitudinal inner bore 74. Body 72 is sized and dimensioned to seat snugly within bore 66 of inflation tube 6. There is a circumferential shoulder 76 inside wall 73 at the approximate mid-point of the wall. As shown, shoulder 76 is beveled, having angled wall 78 on its distal side and a flat face 79 on its proximal side.

There is a reduced outflow valve plunger 80 slidingly engaged in bore 74. As shown, plunger 80 comprises an elongated cylindrical body 82 defining a longitudinal bore 84. There is a circular flange 86 at the distal end of the body. Flange 86 has angled or bevel edge 87 on its distal side and a concentric hole 88 in fluid communication with bore 84. There is a plurality of radial stops 90 at the proximal end of body 82 positioned equal distances around the body. The stops define open airflow passages 92 between the stops.

Figure 32:
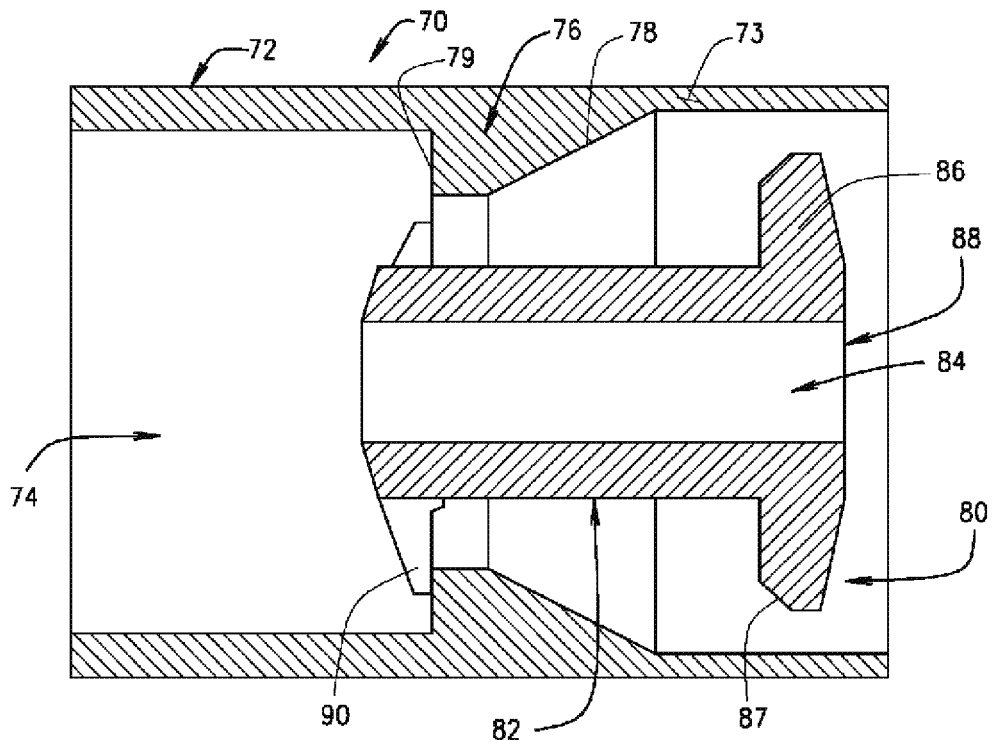
FIG. 32 is an enlarged cross-sectional view of another aspect of the reduced outflow valve in an open position.
Figure 33:
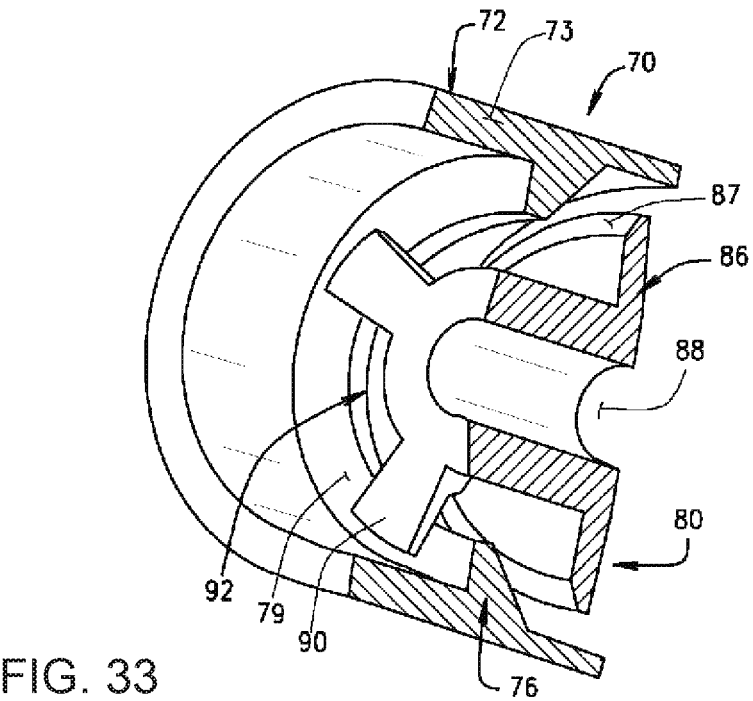
FIG. 33 is a partial proximal end perspective view of the reduced outflow valve of FIG. 32.
Figure 34:
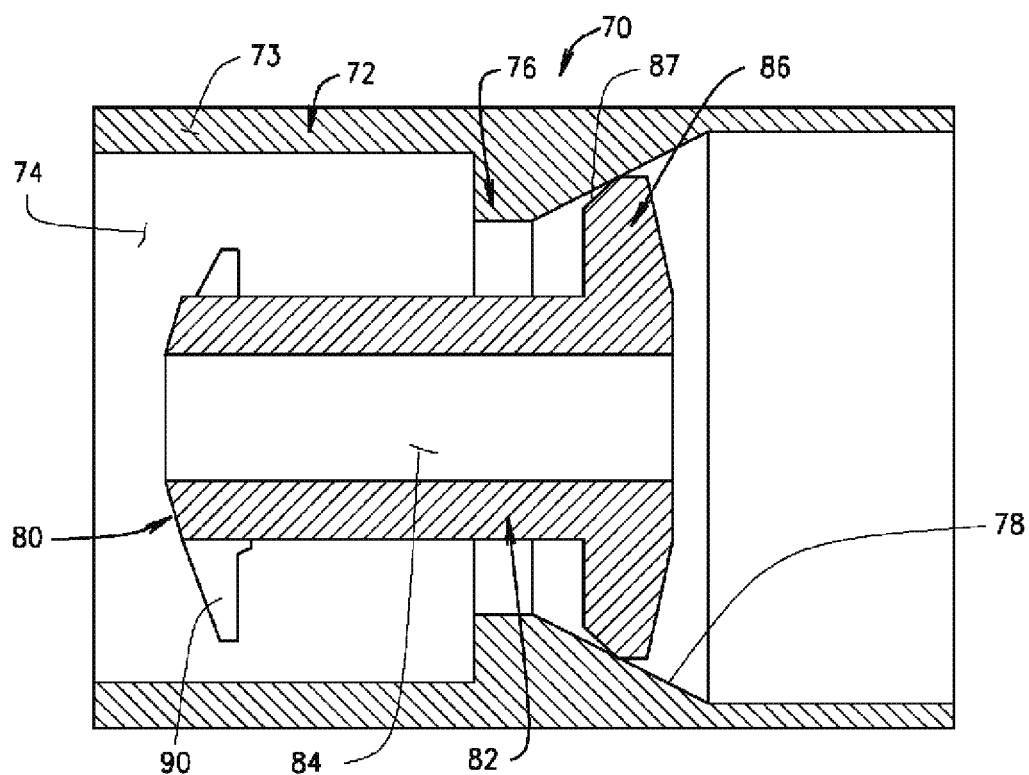
FIG. 34 is a cross-sectional view of the reduced outflow valve of FIG. 9 in a flow restricted position.
Figure 35:
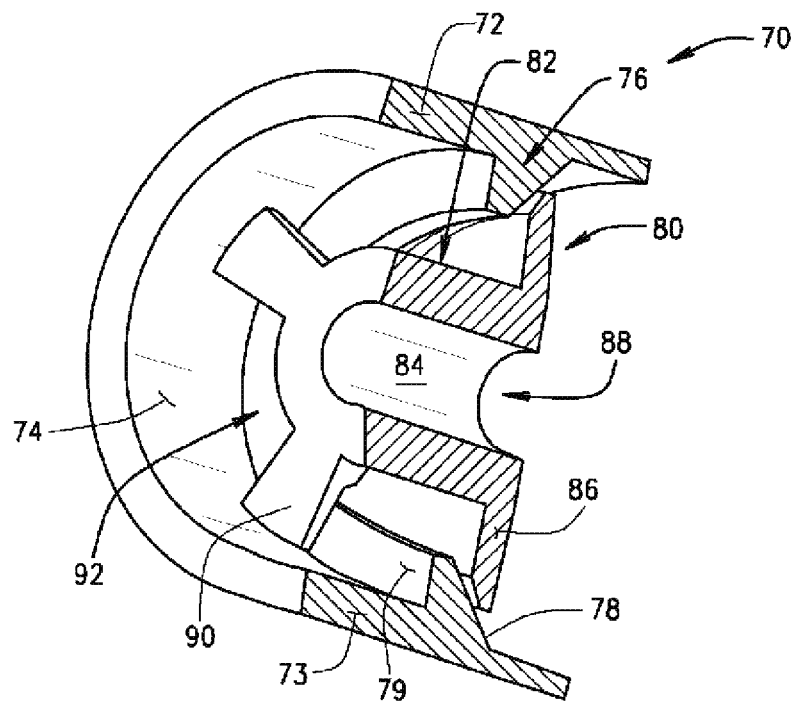
FIG. 35 is a partial proximal end perspective view of the reduced outflow valve of FIG. 34.

As seen in FIGS. 32 and 33, when air is introduced into the inflation tube, plunger 80 is pushed toward the distal end of bore 74. Stops 90 abut flat face 79 of shoulder 76, which halts movement of the plunger. Air flows through airflow passages 92 between the stops and through bore 84 of plunger 80, allowing relatively rapid inflation of the cushion. As best seen in FIGS. 34-35, when the air inflation valve 8 is opened to release air from the cushion, the force of the air moves plunger 80 proximally within bore 74. Beveled edge 87 of flange 86 abuts angled wall 78 on shoulder 76, effectively sealing bore 74 around the flange. Egressing air only can escape through whole 88 and bore 84, thereby damping airflow out of the cushion.

As shown in FIGS. 32 and 34, plunger 80 is totally contained within body 72 in either the first or the second position. It does not extend out of the body. This design prevents the plunger from catching or sticking on the inner air conduit wall and malfunction. All movement of the plunger 80 takes place within bore 74.

Another embodiment of the manifold valve assembly 500 and various components thereof are shown in FIGS. 37A-45C. This embodiment of the manifold valve assembly 500 includes a nozzle assembly 502 and a detachable electronics assembly 504. The nozzle assembly 502 includes a slide housing 506 and one or more connector nipples 507, similar to those in the other embodiments of the valve assembly 100 and 200. The detachable electronics assembly 504 includes one or more printed circuit boards (PCB), one or more transducers, processors, transceivers, gaskets, and power sources, similar to those in the other embodiments of the valve assemblies 100 and 200. In various embodiments, the nozzle assembly 502 is adhered or otherwise fixedly engaged to the cushion 1, while the electronics assembly 504 is removably engaged to the nozzle assembly. When engaged the electronics assembly 504 forms a sealed fluid connection with the nozzle assembly 502.

Figure 38A:
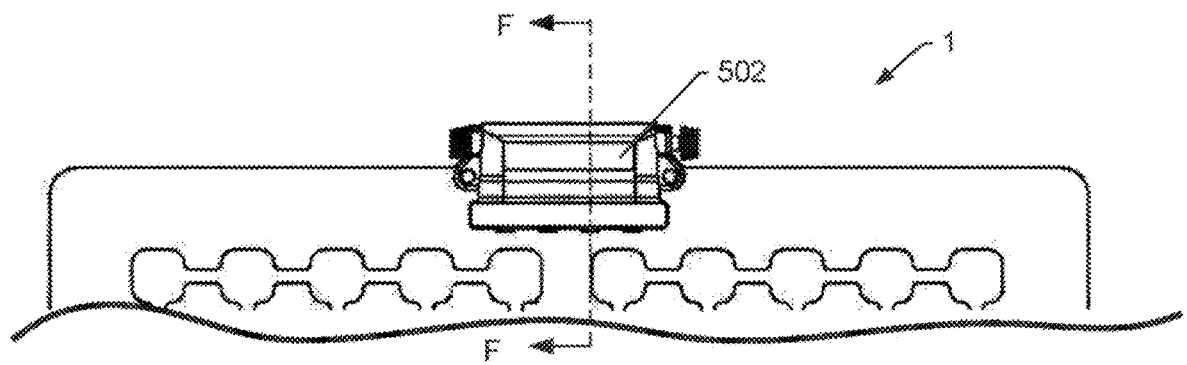
FIG. 38A is a bottom view of a portion zoned cellular cushion engaged to a nozzle assembly with the according to one embodiment.
Figure 38B:
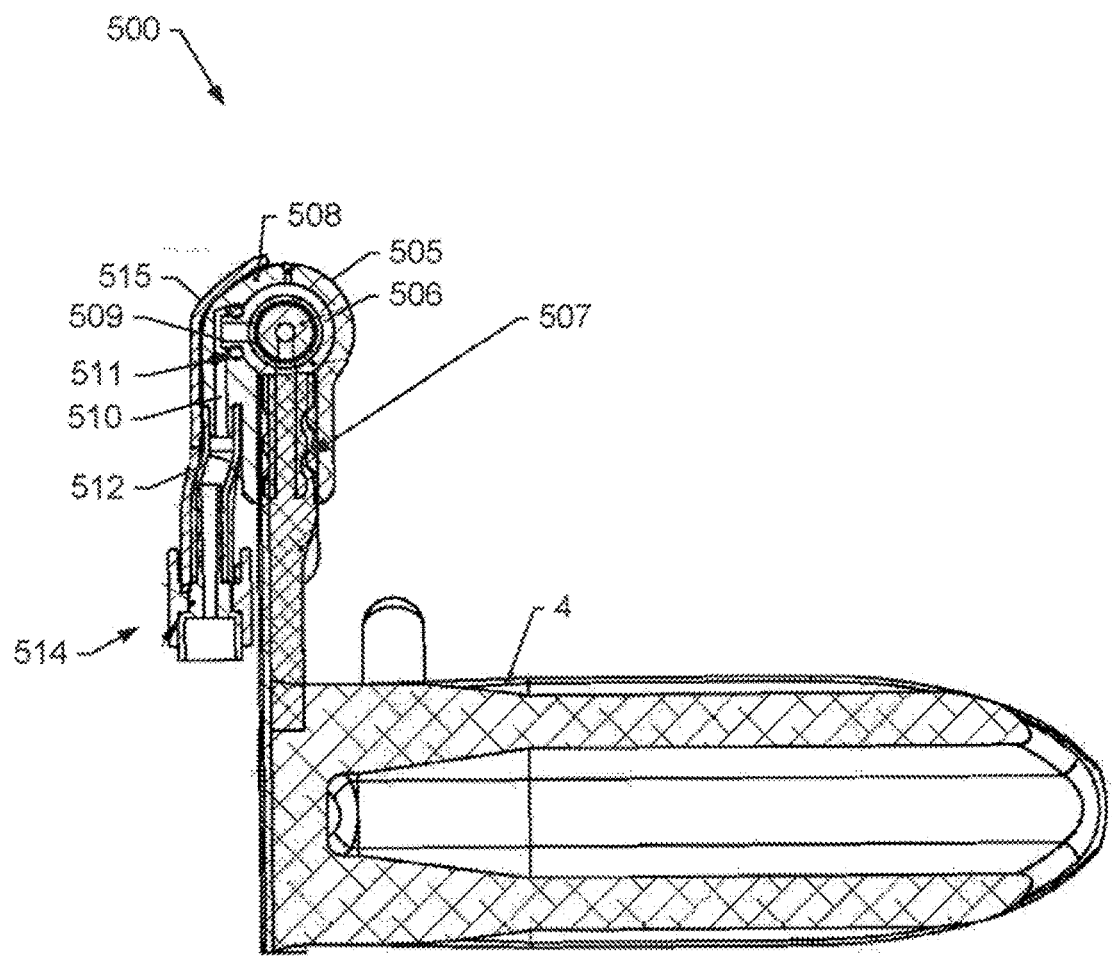
FIG. 38B is a cross-section view of the nozzle assembly engaged to a portion zoned cellular cushion as viewed along line F-F of FIG. 38A.
Figure 39:
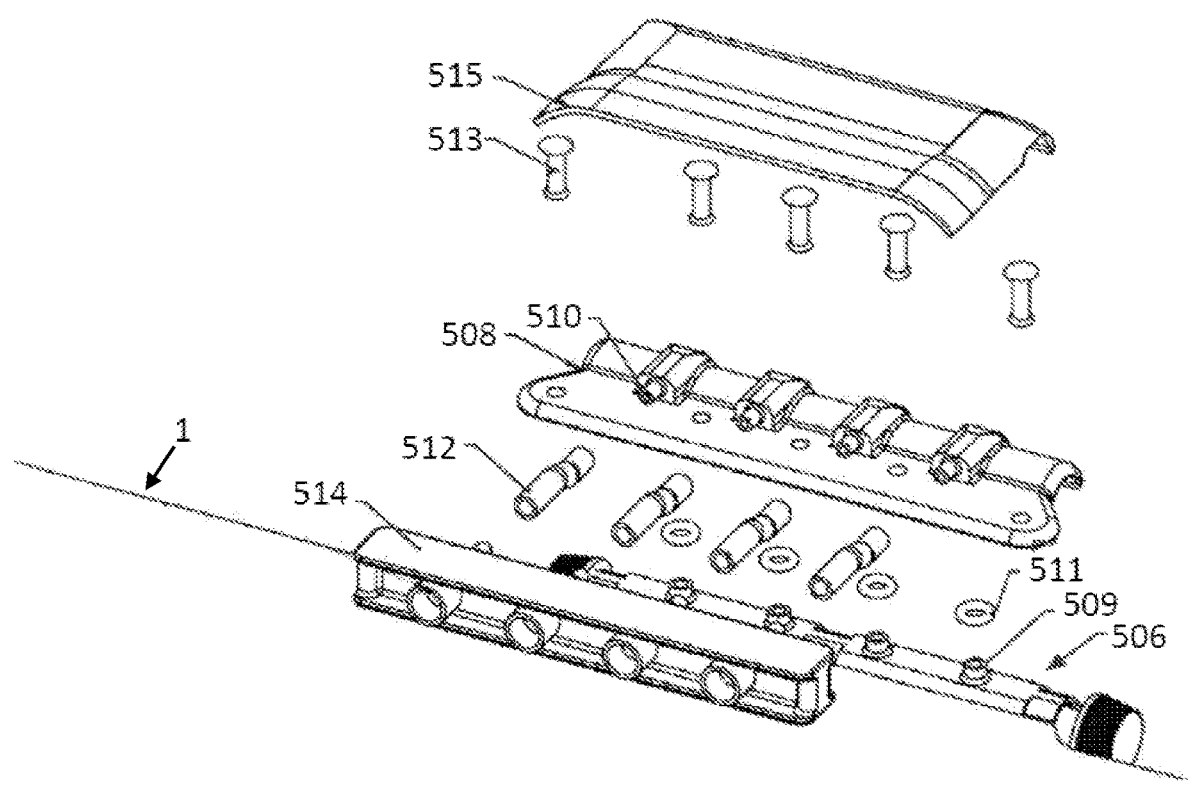
FIG. 39 is an exploded view of the nozzle assembly, according to one embodiment.
Figure 40:
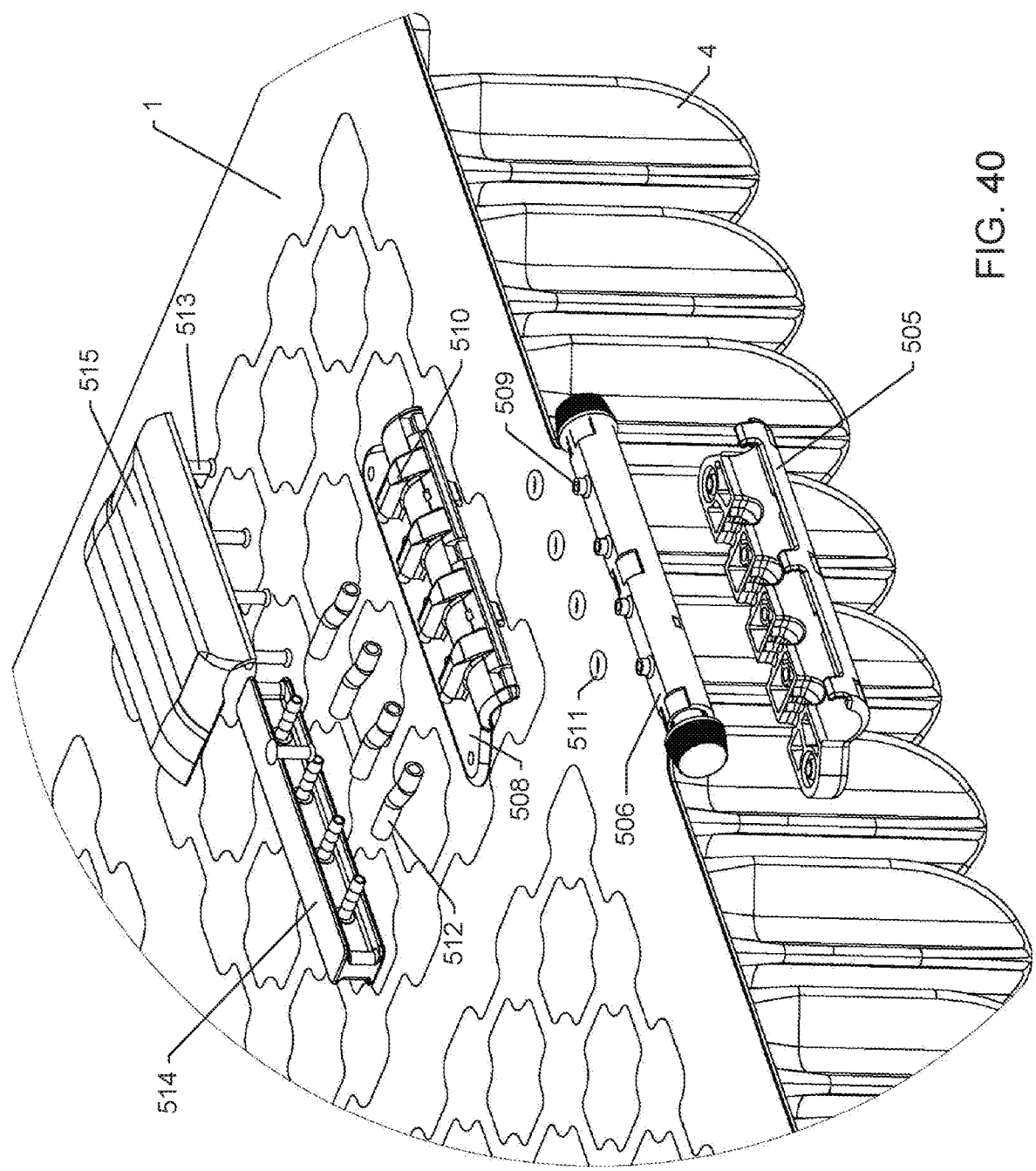
FIG. 40 is another exploded view of the nozzle assembly shown with a portion of a zoned cellular cushion.

FIGS. 38A-B illustrate the nozzle assembly 502 engaged to an embodiment of the cushion 1, while FIGS. 39 and 40 depict the various components of an embodiment of the nozzle assembly. As shown, the nozzle assembly 502 includes slide housing 506, a bottom cover 508, a top cover 505, and one or more cushion connector nipple 507. The cushion connector nipple 507 is substantially similar to the connector nipples 122 and 222. The slide housing 506 is substantially similar to the slide housing 104 and 204; however, the slide housing 506 also defines one or more auxiliary nipples or sensor ports 509. The auxiliary nipple 509 provides a pathway for fluid communication between a corresponding connector nipple 507 and the electronics assembly 504. One or more sealing O-rings 511 are used to maintain an airtight seal between the auxiliary nipples 509 and the bottom cover 508.

As shown, the bottom cover 508 of the nozzle assembly 502 engages the auxiliary nipples 509 and defines a fluid pathway 510 for each auxiliary nipple. In one embodiment, the bottom cover 508 is engaged to the slide housing 506 by fasteners 513 and may, optionally be enclosed by a shroud 515. In various embodiments, each fluid pathway 510 defined by the bottom cover 508 includes barbed fitting to engage a conduit 512. The conduit 512 is further engaged to a valve assembly 514. The valve 514 may be any valve suitable for pressured or unpressured pneumatic connections. In various embodiments, the valve assembly 514 is a quick-connect valve assembly that permits the rapid attachment and detachment of the electronics assembly 504. The valve assembly 514 also provides an airtight seal to the nozzle assembly and ultimately the cushion 1. As such, the cushion may remain in an inflated configuration after detachment of the electronics assembly 504. In one aspect, when the electronics assembly 504 is engaged to the nozzle assembly 502, the air in the cushion is brought into contact with one or more pressure transducer 536 to allow the collection of air pressure readings.

Figure 41A:
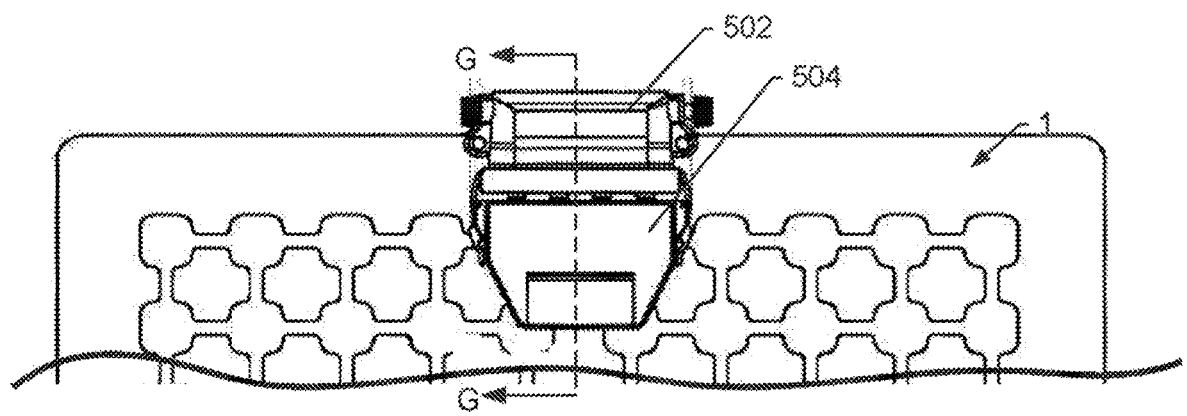
FIG. 41A is a bottom view of a portion zoned cellular cushion engaged to a nozzle assembly and a detachable electronics assembly according to one embodiment.
Figure 41B:
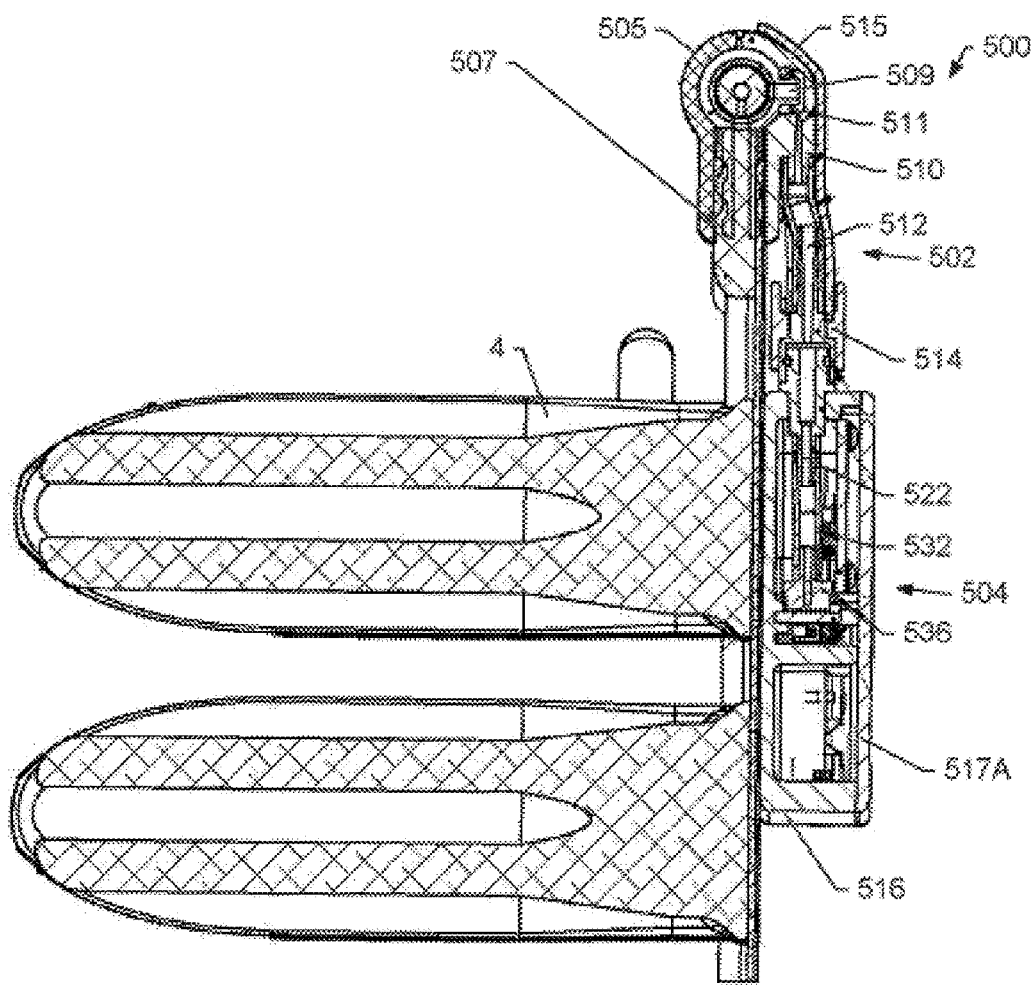
FIG. 41B is a cross-section view of the nozzle assembly and the detachable electronics assembly engaged to a portion zoned cellular cushion as viewed along line G-G of FIG. 41A.
Figure 42E:
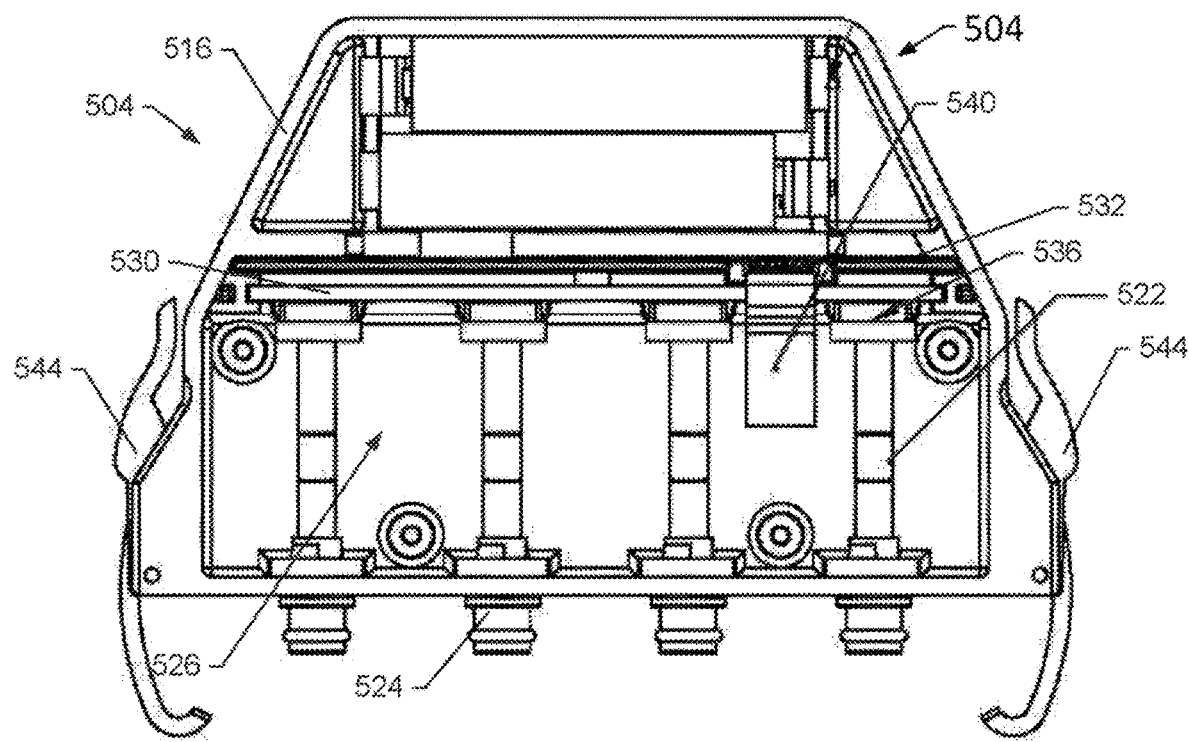
FIGS. 42E and 42F are a top view and perspective view, respectively, of the detachable electronics assembly of FIG. 42A, with the covers removed.
Figure 42F:
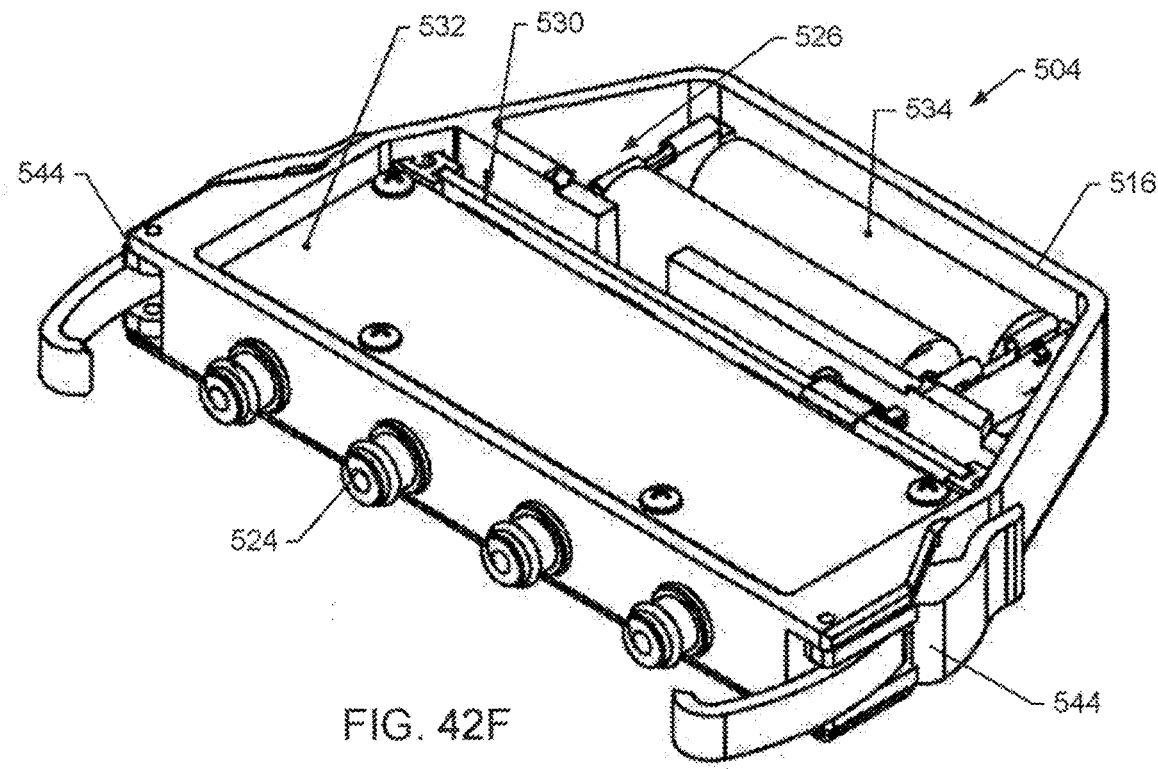
Figure 43:
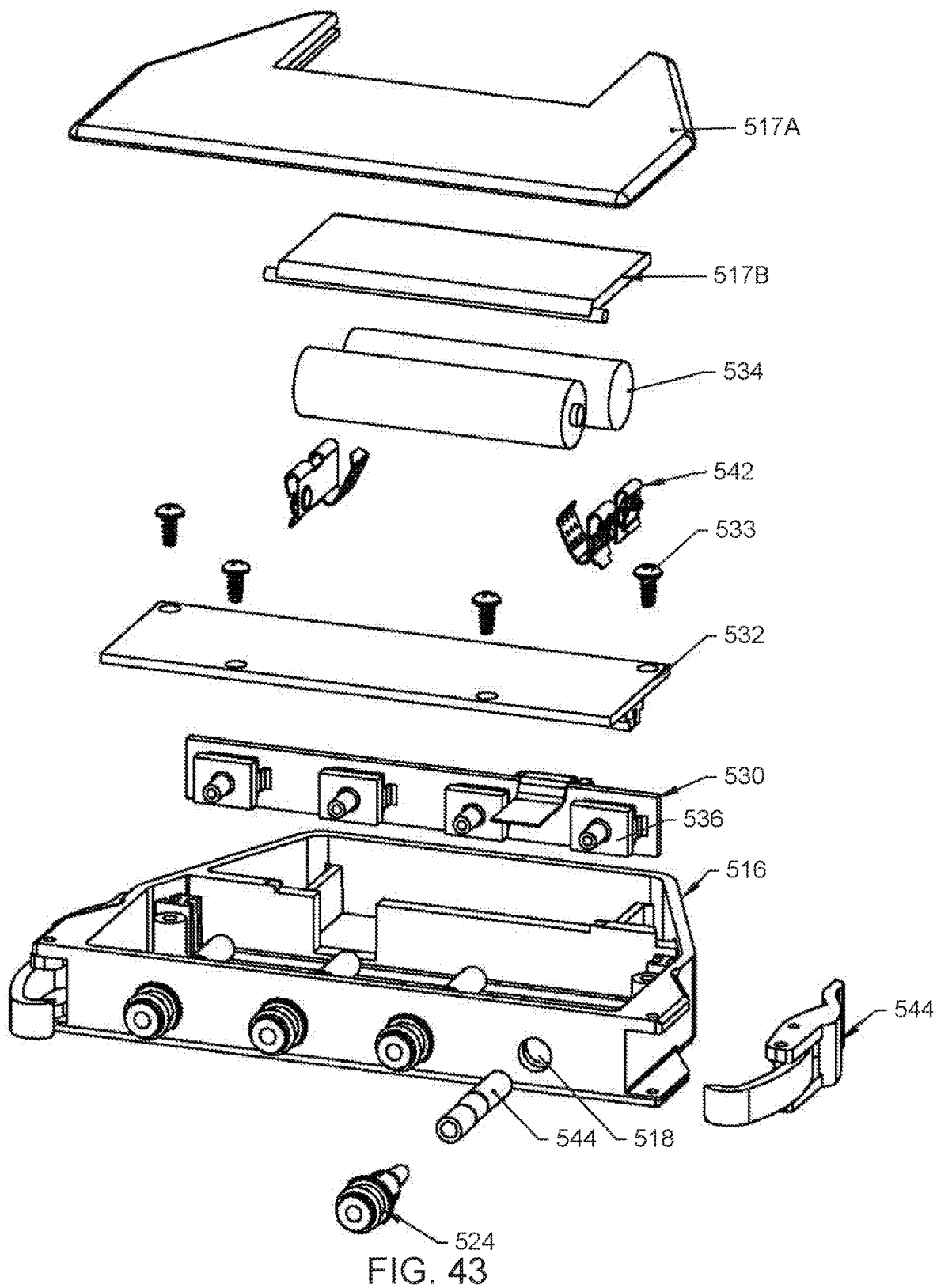
FIG. 43 is an exploded view of the detachable electronics assembly of FIG. 42A.
Figure 44A:
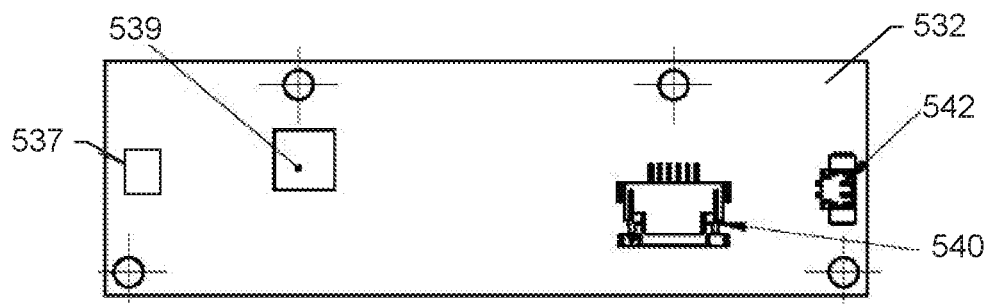
FIGS. 44A and 44B are a top plan view and a front elevation view, respectively, of a main circuit board of the detachable electronics assembly, according to one embodiment.
Figure 44B:
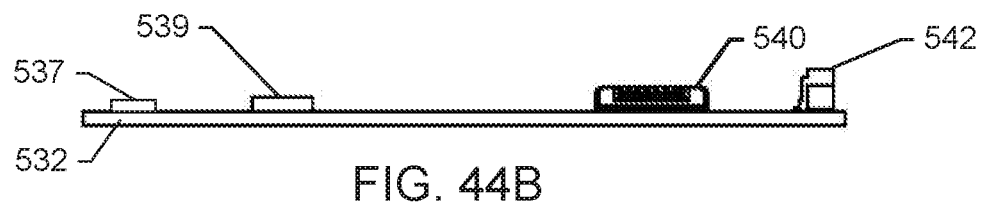
Figure 45A:
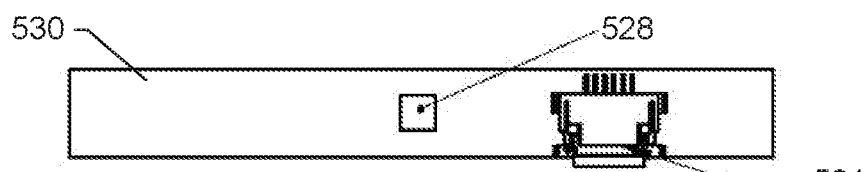
FIGS. 45A, 45B, and 45C are a top plan view, and a side elevation view, and front view, respectively, of a sensor board of the detachable electronics assembly, according to one embodiment.
Figure 45B:
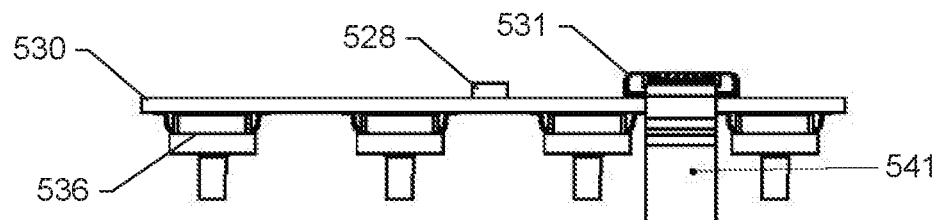
Figure 45C:
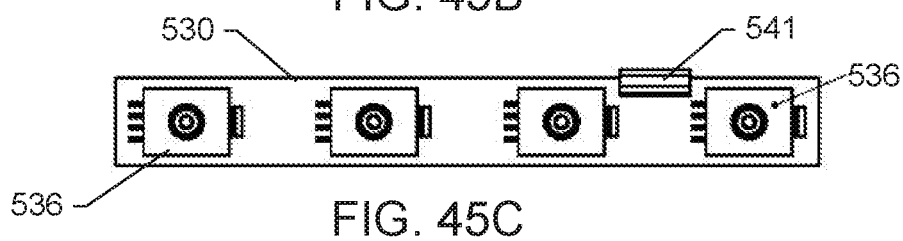

FIGS. 41A-B illustrate the cushion 1 and the nozzle assembly 502 engaged to the electronics assembly 504, while FIGS. 42A-45C depict the various components of the electronics assembly, according to one embodiment. As shown, the electronics assembly 504 includes a housing 516 that includes removable covers 517 A-B. The housing 516 also defines one or more apertures 518 to receive one or more transducer conduit 522 configured to engage the valve assembly 514. By way of example and not limitation, the transducer conduit may further include a seal and a quick-connect connecter 524 configured to engage a quick-connect valve assembly. The housing 516 further defines one or more compartments 526 to receive a sensor board 530, a main circuit board 532, and a power supply 534. The sensor board 530, the main circuit board 532 and the power supply 534 mounted within the electronics enclosure 136 using any suitable means or fastener 533 as understood by one having ordinary skill.

In one embodiment, the sensor board 530 includes one or more pressure transducers 536 and a processor 528. Each pressure transducer 536 is configured to measure the pressure in a corresponding portion of the cushion 1, via the air pathway defined by a corresponding cushion connector nipple 507, auxiliary nipple or sensor port 509, conduit 512, and transducer conduit 522. The data measured at each pressure transducer 536 and processes at the sensor processor 528 is further transmitted to the main circuit board 532 via a sensor communication port 531. In one embodiment, the main circuit board 532 includes a communication device or transceiver 537, such as but not limited to a Bluetooth low energy device (BLE) that may communicate with another computing device, including but not limited to computers, tablets, and smartphones running a compatible application or app. The main circuit board 532 also includes memory, a processor 539, a communication port 540 to communicate with the sensor board 530 via a wired connection 541, gaskets, and a power supply connector 542 to connect to the power supply 534. The power supply is preferably a portable power supply such as one or more battery.

In various embodiments, the processor 539 may detect an optimal immersion depth in response to a signal received from a pressure transducer 536. The signal may correspond to a change in air pressure in at least one zone air conduit. By way of example, the pressure transducer 536 may detect air pressure changes in range of between 0 Pascal (0 mmHg) and 13332.2 Pascal (100 mmHg). Moreover, the pressure transducer is configured to detect an air pressure change as little as 33.3306 Pascal (0.25 mmHg).

The at least one pressure transducer may detect air pressure changes in range of between 0 Pascal (0 mmHg) and 13332.2 Pascal (100 mmHg) and may be configured to detect an air pressure change of at least 33.3306 Pascal (0.25 mmHg). In an aspect, the manifold valve may further include one or more visual indicators.

The housing 516 further includes one or more retention mechanism 544 configured to engage the nozzle assembly 502. In one embodiment, the retention mechanism 544 includes a latch mechanism to engage the valve assembly 514, which aids in providing an airtight connection between the valve assembly 514 and the transducer conduits 522.

Figure 36A:
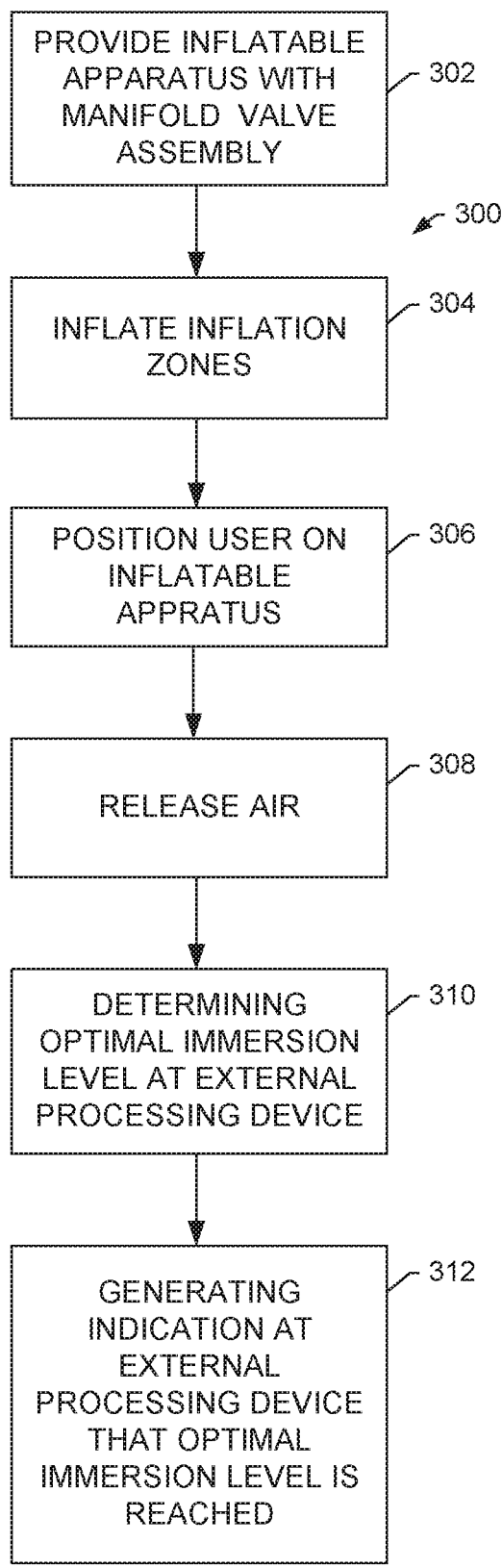
FIGS. 36A-B are flowcharts illustrating methods of using manifold valve assembly for zoned cellular cushions according to one embodiment.

FIG. 36A is a flowchart illustrating one embodiment of a method 300 for using the manifold valve assembly 100 or 200 with an inflatable apparatus having a base and an array of upstanding fluid filled cells. At 302, a manifold valve assembly comprising a valve, an integrated pressure transducer, a processor, and a transceiver is provided. At 304, the inflation zones are inflated, while at 306 a user is positioned on the inflatable apparatus. Air is released from one or more inflation zones at 308, while at 310 an optimal immersion level is determined by comparing pressure data received from the pressure transducer. At 312, a signal is generated to indicate that the optimal immersion level has been reached. In various other embodiments, the methods of using the manifold valve assembly 100 or 200 further include determining the optimal inflation immersion level while the air conduits to each inflation zone are in fluid communication with one another. Once a user is properly positioned, the manifold valve assembly may be actuated to lock or isolate air in one or more of the inflation zones. The method may also include releasing air from one or more inflation zone is released through a reduced outflow valve. In other embodiments, the method 300 may also include observing the visual indicator to determine that the optimal immersion level has been achieved and ceasing the release of air from the at least one inflation zone.

Figure 36B:
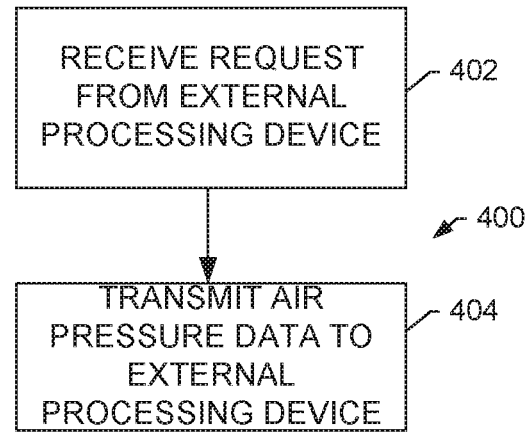
Figure 37A:
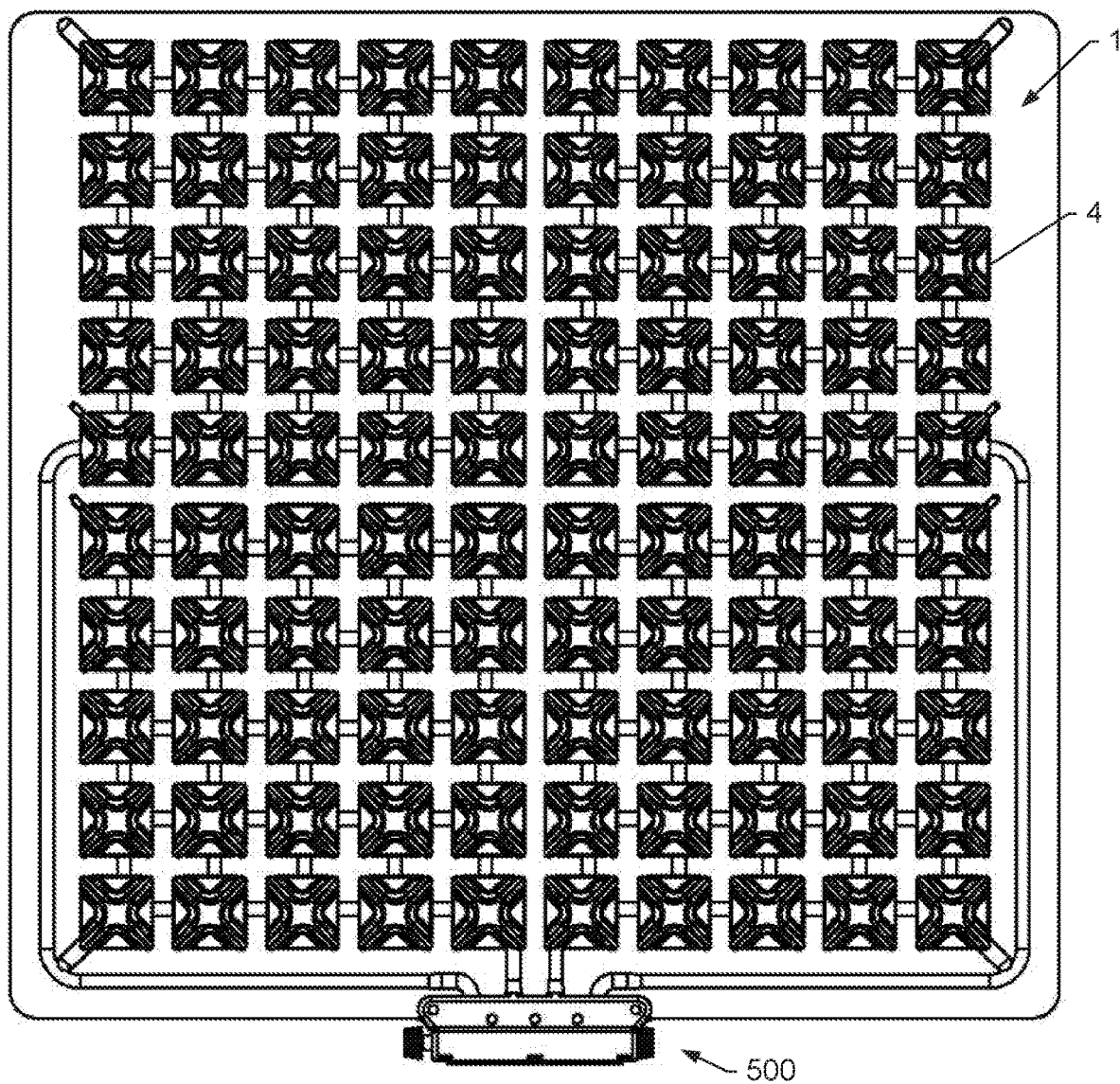
FIG. 37A is a top view of a zoned cellular cushion engaged to another manifold valve assembly according to one embodiment.
Figure 37B:
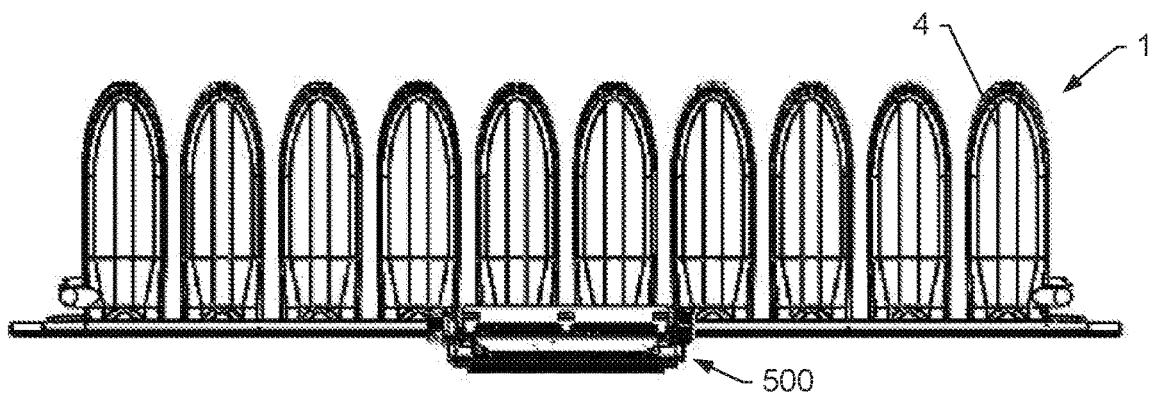
FIG. 37B is a rear view of the zoned cellular cushion engaged to the manifold valve assembly as shown in FIG. 37A.
Figure 37C:
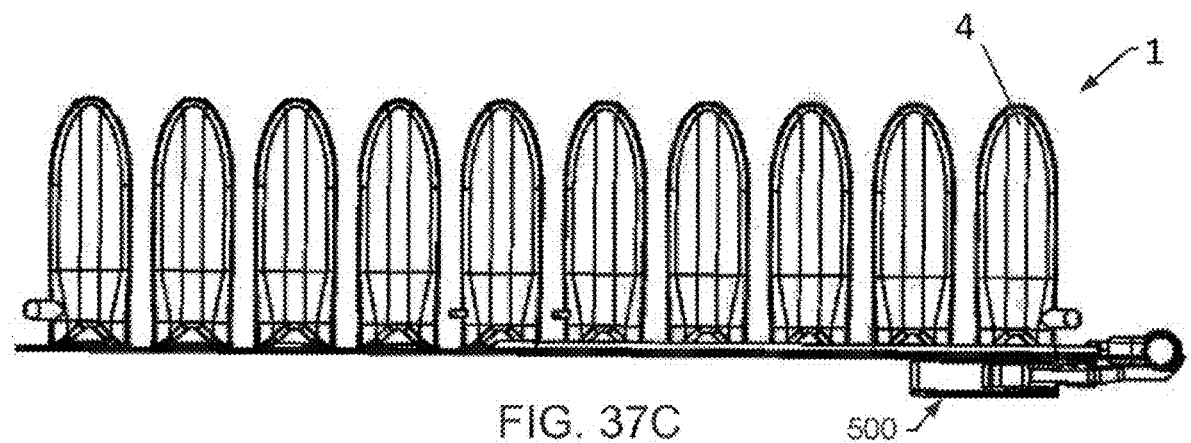
FIG. 37C is a side view of the zoned cellular cushion engaged to the manifold valve assembly as shown in FIG. 37A.
Figure 37D:
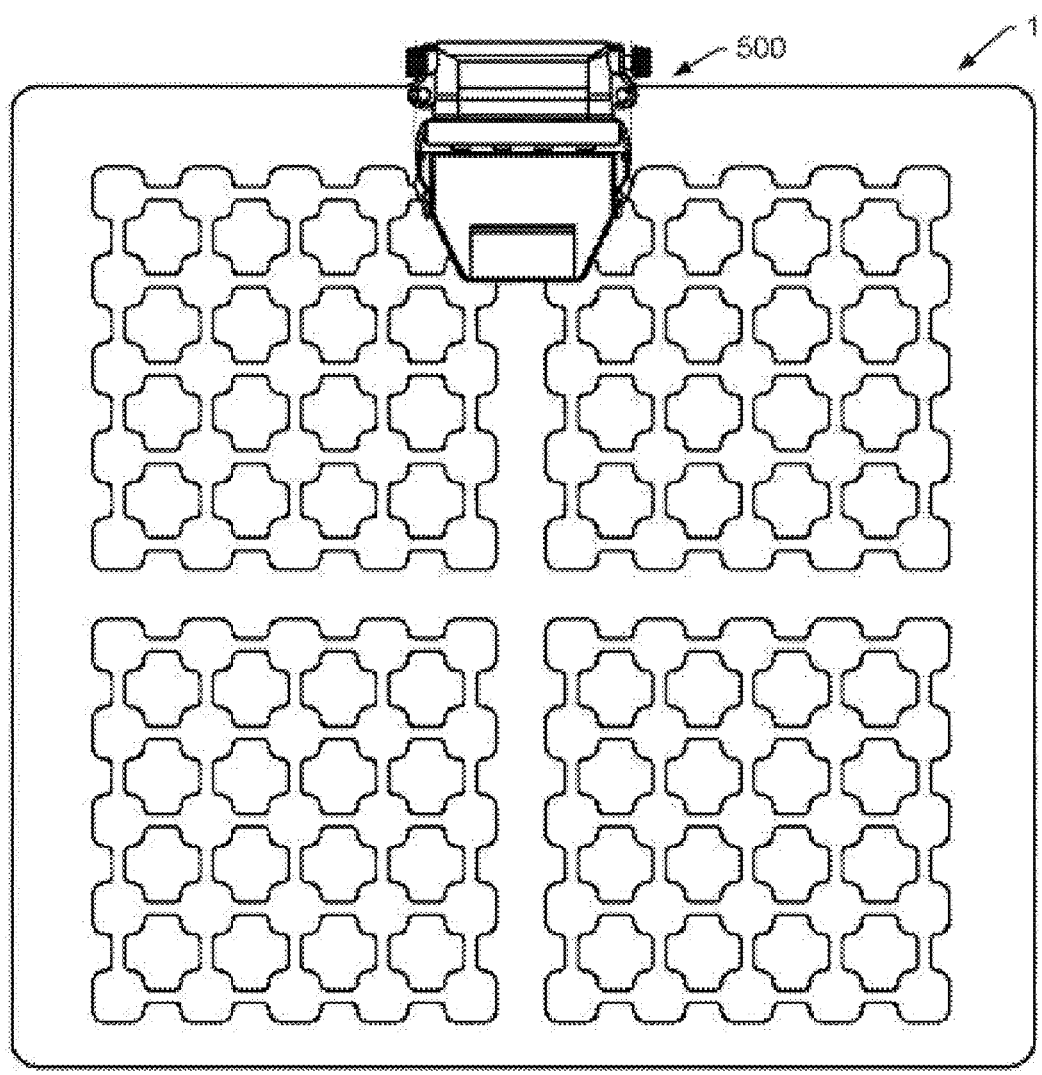
FIG. 37D is a bottom view of the zoned cellular cushion engaged to the manifold valve assembly as shown in FIG. 37A.

FIG. 36B is a flowchart illustrating one embodiment of a method 400 for using the manifold valve assembly 100 or 200 in communication with an external processing device to check an immersion or air pressure inflation level. At 402, the processor and/or transceiver 134 of the manifold valve assembly receives a request signal generated at the external processing device. In one embodiment, the request signal includes a current time and date or other data. At 404, the processor and/or transceiver 134 of the manifold valve assembly transmits current pressure data and other pressure data stored in the memory to the external processing device along with any related historical data to the external processing device. By way of example and not limitation, the historical data may include information regarding previous immersion checks and preferred or optimal immersion levels.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined through components differently in various embodiments of the disclosure or described with different terminology. These and other variations, modifications, additions, and improvements may fall within the scope of the disclosure as defined in the claims that follow.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes.

The invention claimed is:

1. A manifold valve assembly for use with an inflatable apparatus having a base and an array of upstanding fluid filled cells on one side of the base, the array of cells being divided into a plurality of inflation zones, each zone having a separate zone air conduit extending from the zone, the valve assembly comprising:
   a manifold valve comprising:
      a top cover and a bottom cover defining a slide housing seat;
      a slide housing disposed within the slide housing seat, wherein the slide housing is in fluid communication with each zone air conduit, wherein the slide housing includes a slide housing bore and a slide within the slide housing bore;
      a transducer gasket received in a gasket aperture defined by the bottom cover, wherein the transducer gasket defines at least one gasket conduit, wherein the slide housing includes a plurality of connector nipples, each connector nipple includes a connector nipple sensor conduit formed through a sidewall of the connector nipple, and wherein the at least one gasket conduit is in fluid communication with one of the connector nipple sensor conduits; and
   an electronics enclosure engaged to the slide housing, wherein the electronics enclosure houses:
      at least one pressure transducer in fluid communication with the at least one zone air conduit through the gasket conduit and the connector nipple sensor conduit;
      at least one processor;
      at least one transceiver; and
      a power source.

2. The valve assembly of claim 1, wherein the manifold valve is configured to removably engage an inflatable apparatus.

3. The valve assembly of claim 1, wherein the electronics enclosure is removably engaged to the slide housing.

4. The valve assembly of claim 1, wherein the slide housing bore is a longitudinal bore.

5. The valve assembly of claim 1, wherein the slide housing further comprises:
   a wall defining the longitudinal slide housing bore, and at least one connector nipple defining at least one opening through the wall into the longitudinal slide housing bore; and
   the slide received in the longitudinal slide housing bore, and defining at least one slide opening, the slide configured to move axially within the longitudinal slide housing bore,
   wherein movement of the slide within the longitudinal slide housing bore to a first position places the at least one slide opening in functional alignment with the opening of the at least one connector nipple thereby opening the valve, and movement of the slide within the longitudinal slide housing bore to a second position places the at least one slide opening out of functional alignment with the opening of the at least one connector nipple thereby closing the valve.

6. The valve assembly of claim 1, wherein at least one of the transceiver or the processor is a Bluetooth low energy device.

7. The valve assembly of claim 1, wherein the electronics enclosure further includes a memory, and the at least one processor to:
   transmit an indication of pressure in at least one cell of an inflatable apparatus.

8. The valve assembly of claim 7, wherein the processor is configured to receive a signal from the at least one pressure transducer.

9. The valve assembly of claim 8, wherein the signal corresponds to a change in air pressure in at least one zone air conduit.

10. The valve assembly of claim 1, wherein the electronics enclosure further comprises one or more gaskets.

11. The valve assembly of claim 1, wherein the at least one pressure transducer is configured to detect an air pressure change in a range of between 0 Pascal (0 mmHg) and 13332.2 Pascal (100 mmHg).

12. The valve assembly of claim 1, wherein the at least one pressure transducer is configured to detect an air pressure change of at least 33.3306 Pascal (0.25 mmHg).

13. The valve assembly of claim 1, wherein the manifold valve further comprises one or more visual indicators.

* * * * *